US012350362B2

(12) United States Patent
Man et al.

(10) Patent No.: US 12,350,362 B2
(45) Date of Patent: Jul. 8, 2025

(54) FOAMING MIXED ALCOHOL/WATER COMPOSITIONS COMPRISING A COMBINATION OF ALKYL SILOXANE AND A HYDROTROPE/SOLUBILIZER

(71) Applicant: ECOLAB USA INC., Saint Paul, MN (US)

(72) Inventors: Victor Fuk-Pong Man, Saint Paul, MN (US); Gang Pu, Saint Paul, MN (US); Derrick Anderson, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 450 days.

(21) Appl. No.: 17/305,380

(22) Filed: Jul. 6, 2021

(65) Prior Publication Data

US 2022/0000757 A1 Jan. 6, 2022

Related U.S. Application Data

(60) Provisional application No. 62/705,590, filed on Jul. 6, 2020.

(51) Int. Cl.
*C11D 3/37* (2006.01)
*A61K 8/89* (2006.01)
(Continued)

(52) U.S. Cl.
CPC .............. *A61K 8/891* (2013.01); *A61K 8/922* (2013.01); *C08G 77/18* (2013.01); *C11D 3/3738* (2013.01);
(Continued)

(58) Field of Classification Search
CPC ....... C11D 3/162; C11D 3/3723; C11D 3/373; C11D 9/36; B08B 3/04; A61Q 19/00; A61K 8/89; A61K 8/891; A61K 8/92
See application file for complete search history.

(56) References Cited

U.S. PATENT DOCUMENTS

| | | | |
|---|---|---|---|
| 2,096,837 A | 10/1937 | Baker | |
| 2,198,354 A | 4/1940 | Tjaarda | |

(Continued)

FOREIGN PATENT DOCUMENTS

| | | | | |
|---|---|---|---|---|
| BR | 102016000880 | * | 7/2017 | ............... A61K 8/18 |
| BR | 102016000880 A2 | * | 7/2017 | ............... A61K 8/18 |

(Continued)

OTHER PUBLICATIONS

Bergfeld, Wilma F., et al., "Safety Assessment of Alkoxy Polysiloxanes as Used in Cosmetics", Draft Report for Panel Review, pp. 1-235, 2014.
(Continued)

*Primary Examiner* — Brian P Mruk
(74) *Attorney, Agent, or Firm* — McKee, Voorhees & Sease, PLC

(57) ABSTRACT

The disclosure includes synergistic combinations of pendent alkyl siloxanes and PEG-modified castor oils which can form microemulsions and foam in low surface tension solutions. The foaming compositions may form foam in water, alcohol/water, and hydrocarbon condensates. The foaming compositions may replace surfactants in other compositions and forms stable emulsions or microemulsions with oils, including non-trans fats proteins, and fatty acids. The disclosure also includes sterilizing alcohol compositions, cleaning compositions, such as hard surface cleaners, warewash detergents, rinse aids and the like which incorporate the same.

41 Claims, 5 Drawing Sheets

(51) Int. Cl.
| | |
|---|---|
| *A61K 8/891* | (2006.01) |
| *A61K 8/92* | (2006.01) |
| *A61Q 19/00* | (2006.01) |
| *B08B 3/04* | (2006.01) |
| *C08G 77/18* | (2006.01) |
| *C11D 3/382* | (2006.01) |
| *C11D 9/36* | (2006.01) |
| *A61Q 17/00* | (2006.01) |
| *A61Q 19/10* | (2006.01) |

(52) U.S. Cl.
CPC ............ *C11D 3/382* (2013.01); *A61Q 17/005* (2013.01); *A61Q 19/10* (2013.01)

(56) References Cited

U.S. PATENT DOCUMENTS

| | | | |
|---|---|---|---|
| 2,301,989 | A | 11/1942 | Zamborsky |
| 2,367,719 | A | 1/1945 | Gallay |
| 2,396,742 | A | 3/1946 | Milliken |
| 2,410,796 | A | 11/1946 | Newbery et al. |
| 2,436,414 | A | 2/1948 | Arnemo |
| 2,444,870 | A | 7/1948 | Clifford |
| 2,472,564 | A | 6/1949 | Britten, Jr. |
| 2,487,270 | A | 11/1949 | Peterson et al. |
| 2,516,816 | A | 7/1950 | Wagner et al. |
| 2,523,207 | A | 9/1950 | Fowler et al. |
| 2,533,950 | A | 12/1950 | McCormick |
| 2,539,987 | A | 1/1951 | Burger |
| 2,562,329 | A | 7/1951 | O'Brien |
| 2,572,107 | A | 10/1951 | Butin |
| 2,595,025 | A | 4/1952 | Tripplehorn |
| 2,596,994 | A | 5/1952 | Haberland |
| 2,600,854 | A | 6/1952 | Cross |
| 2,647,311 | A | 8/1953 | Arden |
| 3,787,566 | A | 1/1974 | Gauvreau |
| 4,096,240 | A | 6/1978 | Mathur |
| 4,220,665 | A | 9/1980 | Klein |
| 4,258,052 | A | 3/1981 | Yu et al. |
| 4,336,151 | A | 6/1982 | Like et al. |
| 4,511,486 | A | 4/1985 | Shah |
| 4,714,568 | A | 12/1987 | Hurnik et al. |
| 4,725,609 | A | 2/1988 | Kull, Jr. et al. |
| 4,758,599 | A | 7/1988 | Minetti |
| 4,857,302 | A | 8/1989 | Decker, Jr. et al. |
| 5,015,228 | A | 5/1991 | Columbus et al. |
| 5,047,249 | A | 9/1991 | Rothman et al. |
| 5,073,371 | A | 12/1991 | Turner et al. |
| 5,167,950 | A | 12/1992 | Lins |
| D338,585 | S | 8/1993 | Bell et al. |
| 5,250,290 | A | 10/1993 | Giacomoni et al. |
| 5,254,331 | A | 10/1993 | Mausner |
| 5,256,401 | A | 10/1993 | Duckenfield et al. |
| 5,265,772 | A | 11/1993 | Bartasevich et al. |
| 5,266,598 | A | 11/1993 | Ninomiya et al. |
| D343,751 | S | 2/1994 | Bell et al. |
| D346,332 | S | 4/1994 | Kanfer et al. |
| 5,336,497 | A | 8/1994 | Guerrero et al. |
| 5,370,267 | A | 12/1994 | Schroeder |
| 5,441,178 | A | 8/1995 | Wysocki |
| 5,443,236 | A | 8/1995 | Bell et al. |
| 5,449,137 | A | 9/1995 | Bell et al. |
| 5,462,688 | A | 10/1995 | Lippman et al. |
| D365,509 | S | 12/1995 | Bell et al. |
| D365,518 | S | 12/1995 | Wysocki |
| D365,755 | S | 1/1996 | Kanfer et al. |
| 5,523,014 | A | 6/1996 | Dolan et al. |
| 5,558,453 | A | 9/1996 | Bell et al. |
| 5,587,358 | A | 12/1996 | Sukigara et al. |
| 5,625,659 | A | 4/1997 | Sears |
| 5,629,006 | A | 5/1997 | Hoang et al. |
| 5,635,462 | A | 6/1997 | Fendler et al. |
| D383,001 | S | 9/1997 | Bell et al. |
| D385,795 | S | 11/1997 | Wysocki et al. |
| 5,718,353 | A | 2/1998 | Kanfer et al. |
| 5,719,113 | A | 2/1998 | Fendler et al. |
| D392,136 | S | 3/1998 | Ross et al. |
| 5,725,131 | A | 3/1998 | Bell et al. |
| D400,799 | S | 11/1998 | Bell et al. |
| 5,833,998 | A | 11/1998 | Biedermann et al. |
| 5,853,700 | A | 12/1998 | Gormley et al. |
| 5,880,088 | A | 3/1999 | Lentsch et al. |
| 5,902,778 | A | 5/1999 | Hartmann et al. |
| D411,456 | S | 6/1999 | Mast et al. |
| 5,939,082 | A | 8/1999 | Oblong et al. |
| 5,944,227 | A | 8/1999 | Schroeder et al. |
| D415,343 | S | 10/1999 | Maddox |
| 5,962,482 | A | 10/1999 | Bissett |
| 5,968,528 | A | 10/1999 | Deckner et al. |
| 5,972,356 | A | 10/1999 | Peffly et al. |
| D416,417 | S | 11/1999 | Ross et al. |
| 5,980,921 | A | 11/1999 | Biedermann et al. |
| 5,989,523 | A | 11/1999 | Fitzjarrell |
| 5,996,851 | A | 12/1999 | Dolan et al. |
| 5,997,887 | A | 12/1999 | Ha et al. |
| 5,997,890 | A | 12/1999 | Sine et al. |
| D418,708 | S | 1/2000 | Kanfer et al. |
| 6,022,551 | A | 2/2000 | Jampani et al. |
| 6,024,942 | A | 2/2000 | Tanner et al. |
| D422,828 | S | 4/2000 | Kanfer et al. |
| 6,046,152 | A | 4/2000 | Vinson et al. |
| 6,065,639 | A | 5/2000 | Maddox et al. |
| 6,087,309 | A | 7/2000 | Vinson et al. |
| 6,090,395 | A | 7/2000 | Asmus et al. |
| 6,130,253 | A | 10/2000 | Franklin et al. |
| 6,149,925 | A | 11/2000 | Mammone et al. |
| 6,183,766 | B1 | 2/2001 | Sine et al. |
| 6,217,885 | B1 | 4/2001 | Röder et al. |
| 6,224,888 | B1 | 5/2001 | Vatter et al. |
| 6,239,093 | B1 | 5/2001 | Foley et al. |
| 6,265,363 | B1 | 7/2001 | Viscovitz |
| 6,267,976 | B1 | 7/2001 | Barnhart et al. |
| 6,274,124 | B1 | 8/2001 | Vollhardt |
| 6,309,657 | B2 | 10/2001 | Vatter et al. |
| 6,319,958 | B1 | 11/2001 | Johnson et al. |
| 6,333,039 | B1 | 12/2001 | Fendler et al. |
| 6,344,218 | B1 | 2/2002 | Dodd et al. |
| 6,352,701 | B1 | 3/2002 | Scholz et al. |
| 6,383,505 | B1 | 5/2002 | Kaiser et al. |
| 6,383,997 | B1 | 5/2002 | McManus |
| 6,407,051 | B1 | 6/2002 | Smith et al. |
| 6,423,329 | B1 | 7/2002 | Sine et al. |
| 6,432,430 | B1 | 8/2002 | Fitzjarrell |
| 6,462,010 | B1 | 10/2002 | Aszman et al. |
| 6,528,070 | B1 | 3/2003 | Bratescu et al. |
| 6,534,069 | B1 | 3/2003 | Asmus et al. |
| 6,592,880 | B1 | 7/2003 | Jager |
| 6,607,737 | B2 | 8/2003 | Bekele et al. |
| 6,613,341 | B2 | 9/2003 | Motley et al. |
| 6,623,744 | B2 | 9/2003 | Asmus et al. |
| 6,689,593 | B2 | 2/2004 | Millis et al. |
| 6,706,679 | B1 | 3/2004 | Bergeron et al. |
| 6,709,647 | B2 | 3/2004 | Bhakoo et al. |
| 6,723,689 | B1 | 4/2004 | Hoang et al. |
| 6,846,846 | B2 | 1/2005 | Modak et al. |
| 6,903,064 | B1 | 6/2005 | Kasturi et al. |
| 6,939,552 | B2 | 9/2005 | Ansara et al. |
| 6,977,082 | B2 | 12/2005 | Seitz, Jr. et al. |
| 6,979,468 | B1 | 12/2005 | Pollard |
| 7,081,246 | B2 | 7/2006 | Asmus et al. |
| 7,166,435 | B2 | 1/2007 | Rosenbloom |
| 7,199,090 | B2 | 4/2007 | Koivisto et al. |
| 7,465,697 | B1 | 12/2008 | DeAth |
| 7,560,422 | B2 | 7/2009 | Shapiro |
| 7,569,530 | B1 | 8/2009 | Pan et al. |
| 7,612,115 | B2 | 11/2009 | Suzuki et al. |
| 7,651,990 | B2 | 1/2010 | Asmus |
| 7,795,196 | B2 | 9/2010 | Luu et al. |
| 7,803,390 | B2 | 9/2010 | Asmus et al. |
| 7,842,725 | B2 | 11/2010 | Wegner et al. |
| 7,914,774 | B2 | 3/2011 | Meehan |
| 8,058,315 | B2 | 11/2011 | Wegner et al. |
| 8,106,094 | B2 | 1/2012 | Sah et al. |
| 8,119,698 | B2 | 2/2012 | Polonka et al. |

(56) References Cited

U.S. PATENT DOCUMENTS

| | | |
|---|---|---|
| 8,263,098 B2 | 9/2012 | Fernandez de Castro et al. |
| 8,309,111 B2 | 11/2012 | Fernandez de Castro et al. |
| 8,313,758 B2 | 11/2012 | Fernandez de Castro et al. |
| 8,333,954 B2 | 12/2012 | Seidling et al. |
| 8,383,686 B2 | 2/2013 | Wegner et al. |
| 8,530,524 B2 | 9/2013 | Wegner et al. |
| 8,658,701 B2 | 2/2014 | Wegner et al. |
| 8,697,622 B2 | 4/2014 | Man et al. |
| 8,940,797 B2 | 1/2015 | Wegner et al. |
| 9,414,586 B2 | 8/2016 | Wegner et al. |
| 2002/0022660 A1 | 2/2002 | Jampani et al. |
| 2002/0168329 A1 | 11/2002 | Kini et al. |
| 2003/0023550 A1 | 1/2003 | Lee |
| 2003/0049212 A1 | 3/2003 | Robinson et al. |
| 2003/0147925 A1 | 8/2003 | Sawan et al. |
| 2003/0194447 A1 | 10/2003 | Scholz et al. |
| 2003/0203452 A1 | 10/2003 | Li et al. |
| 2003/0211066 A1 | 11/2003 | Scholz et al. |
| 2003/0215418 A1 | 11/2003 | Asmus et al. |
| 2004/0001797 A1 | 1/2004 | Saud et al. |
| 2004/0102429 A1 | 5/2004 | Modak et al. |
| 2004/0191274 A1 | 9/2004 | Grayson et al. |
| 2004/0247685 A1 | 12/2004 | Modak et al. |
| 2005/0053593 A1 | 3/2005 | Wang et al. |
| 2005/0058673 A1 | 3/2005 | Scholz et al. |
| 2005/0089539 A1 | 4/2005 | Scholz et al. |
| 2005/0102266 A1 | 5/2005 | Nason et al. |
| 2005/0142079 A1 | 6/2005 | Garrison et al. |
| 2005/0148059 A1 | 7/2005 | Estell et al. |
| 2006/0014750 A1 | 1/2006 | O'Donnell et al. |
| 2006/0035807 A1 | 2/2006 | Kasturi et al. |
| 2006/0051384 A1 | 3/2006 | Scholz et al. |
| 2006/0062832 A1 | 3/2006 | Lopes |
| 2006/0094387 A1 | 5/2006 | Darabi |
| 2006/0104911 A1 | 5/2006 | Novak |
| 2006/0104919 A1 | 5/2006 | Novak |
| 2006/0177511 A1 | 8/2006 | Scholz et al. |
| 2006/0182690 A1 | 8/2006 | Veeger et al. |
| 2006/0193745 A1 | 8/2006 | Arndt et al. |
| 2006/0193789 A1 | 8/2006 | Tamarkin et al. |
| 2006/0221103 A1 | 10/2006 | Takanose et al. |
| 2006/0222502 A1 | 10/2006 | Hansen et al. |
| 2006/0229364 A1 | 10/2006 | Hobbs et al. |
| 2006/0235798 A1 | 10/2006 | Alkove et al. |
| 2006/0281663 A1 | 12/2006 | Asmus |
| 2007/0027055 A1 | 2/2007 | Koivisto et al. |
| 2007/0065383 A1 | 3/2007 | Fernandez de Castro et al. |
| 2007/0076125 A1 | 4/2007 | Choi et al. |
| 2007/0148101 A1 | 6/2007 | Snyder et al. |
| 2007/0179207 A1 | 8/2007 | Fernandez de Castro et al. |
| 2007/0184013 A1 | 8/2007 | Snyder et al. |
| 2007/0184016 A1 | 8/2007 | Macinga et al. |
| 2007/0185216 A1 | 8/2007 | Snyder et al. |
| 2007/0190177 A1 | 8/2007 | Kling et al. |
| 2007/0237807 A1 | 10/2007 | Luu et al. |
| 2007/0258911 A1 | 11/2007 | Fernandez de Castro et al. |
| 2007/0274926 A1 | 11/2007 | Fuls et al. |
| 2007/0274940 A1 | 11/2007 | Fuls et al. |
| 2007/0275929 A1 | 11/2007 | Fuls et al. |
| 2007/0280900 A1 | 12/2007 | Fox et al. |
| 2007/0280901 A1 | 12/2007 | Fuls et al. |
| 2007/0281039 A1 | 12/2007 | DeAth |
| 2007/0281999 A1 | 12/2007 | Fox et al. |
| 2008/0004449 A1 | 1/2008 | Yong et al. |
| 2008/0026974 A1 | 1/2008 | Barnhart et al. |
| 2008/0044479 A1 | 2/2008 | Stack |
| 2008/0095814 A1 | 4/2008 | Taylor et al. |
| 2008/0108704 A1 | 5/2008 | Asmus et al. |
| 2008/0121355 A1 | 5/2008 | Pylkki et al. |
| 2008/0138438 A1 | 6/2008 | Taylor et al. |
| 2008/0139656 A1 | 6/2008 | Taylor et al. |
| 2008/0142023 A1 | 6/2008 | Schmid et al. |
| 2008/0145390 A1 | 6/2008 | Taylor et al. |
| 2008/0199535 A1 | 8/2008 | Taylor et al. |
| 2008/0200890 A1 | 8/2008 | Wood et al. |
| 2008/0207767 A1 | 8/2008 | Dobos et al. |
| 2008/0213198 A1 | 9/2008 | Lintner et al. |
| 2008/0213595 A1 | 9/2008 | Levitt et al. |
| 2008/0249187 A1 | 10/2008 | Ali et al. |
| 2008/0254150 A1 | 10/2008 | Rheins et al. |
| 2008/0286223 A1 | 11/2008 | Fuls et al. |
| 2008/0287538 A1 | 11/2008 | Scholz et al. |
| 2009/0009806 A1 | 1/2009 | Matsuda |
| 2009/0012174 A1 | 1/2009 | Seitz, Jr. et al. |
| 2009/0018213 A1 | 1/2009 | Snyder et al. |
| 2009/0023890 A1 | 1/2009 | Monahan et al. |
| 2009/0046116 A1 | 2/2009 | Davies et al. |
| 2009/0062176 A1 | 3/2009 | Seidling et al. |
| 2009/0095821 A1 | 4/2009 | Feriani et al. |
| 2009/0104281 A1 | 4/2009 | Taylor et al. |
| 2009/0117061 A1 | 5/2009 | Gross |
| 2009/0191248 A1 | 7/2009 | Hoffman et al. |
| 2009/0202463 A1 | 8/2009 | Pan et al. |
| 2009/0214628 A1 | 8/2009 | de Rijk |
| 2009/0226541 A1 | 9/2009 | Scholz et al. |
| 2009/0252775 A1 | 10/2009 | Arndt et al. |
| 2009/0265230 A1 | 10/2009 | Plachouras et al. |
| 2009/0281021 A1 | 11/2009 | Venkataraman et al. |
| 2009/0304812 A1 | 12/2009 | Staniforth et al. |
| 2009/0324661 A1 | 12/2009 | Polonka et al. |
| 2009/0326076 A1 | 12/2009 | Asmus |
| 2010/0003198 A1 | 1/2010 | Stolmeier et al. |
| 2010/0022654 A1 | 1/2010 | Asmus et al. |
| 2010/0029780 A1 | 2/2010 | Grayson et al. |
| 2010/0069505 A1 | 3/2010 | Veeger et al. |
| 2010/0124280 A1 | 5/2010 | Chujoh et al. |
| 2010/0160453 A1 | 6/2010 | Koivisto et al. |
| 2010/0204323 A1 | 8/2010 | Theiler et al. |
| 2010/0282409 A1 | 11/2010 | Hobbs et al. |
| 2010/0305211 A1 | 12/2010 | Modak et al. |
| 2010/0317743 A1 | 12/2010 | Macinga et al. |
| 2010/0327013 A1 | 12/2010 | Asmus |
| 2010/0331411 A1 | 12/2010 | Asmus |
| 2010/0331422 A1 | 12/2010 | Asmus et al. |
| 2011/0104079 A1 | 5/2011 | Snyder et al. |
| 2011/0110869 A1 | 5/2011 | Scholz et al. |
| 2011/0144214 A1 | 6/2011 | Snyder et al. |
| 2011/0224144 A1 | 9/2011 | Akil et al. |
| 2011/0230395 A1 | 9/2011 | Otto et al. |
| 2011/0274770 A1 | 11/2011 | Scholz et al. |
| 2012/0011468 A1 | 1/2012 | Zhang |
| 2012/0053108 A1 | 3/2012 | Glenn, Jr. et al. |
| 2012/0121725 A1 | 5/2012 | Garnier et al. |
| 2012/0164087 A1 | 6/2012 | Carter |
| 2012/0189684 A1 | 7/2012 | Buckley et al. |
| 2012/0208894 A1 | 8/2012 | Kampf et al. |
| 2013/0303725 A1 | 11/2013 | Dobrawa et al. |
| 2014/0148374 A1 | 5/2014 | Man et al. |
| 2014/0332562 A1 | 11/2014 | Seidling et al. |
| 2014/0364509 A1 | 12/2014 | Wegner et al. |
| 2015/0203443 A1 | 7/2015 | Klostermann et al. |
| 2016/0015031 A1 | 1/2016 | Pesaro et al. |
| 2016/0346178 A1 | 12/2016 | Wegner et al. |
| 2020/0131453 A1 | 4/2020 | Dahlquist et al. |
| 2021/0009923 A1 | 1/2021 | Miller et al. |

FOREIGN PATENT DOCUMENTS

| | | | |
|---|---|---|---|
| DE | 19523320 A1 | 1/1997 | |
| EP | 0396442 A1 | 11/1990 | |
| EP | 0849070 A1 | 6/1998 | |
| EP | 0882446 A1 | 12/1998 | |
| EP | 0888434 B1 | 1/1999 | |
| EP | 1557160 A1 | 7/2005 | |
| EP | 1811013 B1 | 7/2007 | |
| EP | 2412791 A1 | 2/2012 | |
| EP | 2851416 B1 | 3/2015 | |
| EP | 3292757 A1 | 3/2018 | |
| GB | 2516261 | * 1/2015 | ............... C11D 1/66 |
| GB | 2516261 A | 1/2015 | |
| JP | 3179098 A | 8/1991 | |
| JP | H03204809 A | 9/1991 | |
| JP | 748245 A | 2/1995 | |
| JP | 7179332 A | 7/1995 | |

(56) References Cited

FOREIGN PATENT DOCUMENTS

| | | |
|---|---|---|
| JP | 7206634 A | 8/1995 |
| JP | H10167938 A | 6/1998 |
| JP | 2003012466 A | 1/2003 |
| JP | 2018002683 A | 1/2018 |
| JP | 2018008934 A | 1/2018 |
| KR | 101366211 B1 | 2/2014 |
| WO | 0135905 A2 | 5/2001 |
| WO | 2003076117 A1 | 9/2003 |
| WO | 2003084486 A1 | 10/2003 |
| WO | 2003095600 A1 | 11/2003 |
| WO | 2005051341 A1 | 6/2005 |
| WO | 2006038019 A1 | 4/2006 |
| WO | 2006094387 A1 | 9/2006 |
| WO | 2006138111 A1 | 12/2006 |
| WO | 2009027867 A3 | 3/2009 |
| WO | 2011123727 A2 | 10/2011 |
| WO | 2013124784 A1 | 8/2013 |
| WO | 2015061552 A1 | 4/2015 |
| WO | 2016085906 A1 | 6/2016 |
| WO | 2017199004 A1 | 11/2017 |

OTHER PUBLICATIONS

Brehm-Stecher, Johnson, "Sensitization of *Staphylococcus aureus* and *Escherichia coli* to Antibiotics by the Sesquiterpenoids Nerolidol, Farnesol, Bisabolol, and Apritone", University of Wisconsin-Madison, Antimicrobial Agents and Chemotherapy, vol. 47, No. 10, pp. 3357-3360, Oct. 2003.
Cosmocil (Tm) Folder, 5 pages, Jun. 9, 2014.
Intrinsic Activity of Cosmocil CQ, Avecia, 2 pages, Jun. 9, 2014.
Morton, H., "The relationship of concentration and germicidal efficiency of ethyl alcohol", Annals New York Academy of Sciences, vol. 52, XP008066591, pp. 191-196, Dec. 31, 1950.
Australian Government, "Patent Examination Report No. 1", issued in connection with Patent Application 2009275235, 4 pages, mailed Oct. 29, 2014.
Australian Government, "Patent Examination Report No. 2", issued in connection with Patent Application No. 2009275235, 4 pages, mailed Feb. 27, 2015.
O'Lenick, Tony, "Bis-PEG vs. PEG dimethicone", Cosmetics and Toiletries, http://www.cosmeticsandtoiletries.com/research/chemistry/7847427, 2 pages, 2007.
Schloss Man, M. (Ed.): "The chemistry and manufacture of cosmetics: Formulating, vol. 2, Ed. 3", Allured Pub., USA 277870, XP002390779, pp. 237-239, Dec. 31, 2000.
PEL-SIL™ bis-PEG-12 Datasheet, Ele Corporation, 3 pages, Oct. 10, 2019.
Technical Information from BASF for Bisabolol, 8 pages, Nov. 30, 2002.
Technical Specification for Farnesol, Symrise, 2 pages, Jun. 1, 2004.
Worldwide Healthcare Inc., "Material Safety Data Sheet", 2 pages, Jan. 24, 2007.
European Patent Office, "Supplementary European Search Report", issued in connection with Application No./ Patent No. 11796409.8-1354 / 2802636 PCT/US20211040626, 7 pages, mailed Dec. 9, 2014.
International Searching Authority in connection with PCT/US2021/040526 filed Jul. 6, 2021, "The International Search Report and the Written Opinion of the International Searching Authority, or the Declaration", mailed Nov. 5, 2021.
International Searching Authority in connection with PCT/US2021/040506 filed Jul. 6, 2021, "The International Search Report and the Written Opinion of the International Searching Authority, or the Declaration", 15 pages, mailed Nov. 4, 2021.
International Searching Authority in connection with PCT/US2021/040531 filed Jul. 6, 2021, "The International Search Report and the Written Opinion of the International Searching Authority, or the Declaration", 11 pages, mailed Oct. 19, 2021.
Siltech Corporation, "Innovative Silicone Specialties," Siltech, 2008, Product Brochure, 20 pages.
Siltech Corporation, "Silsurf® Di-2012," Siltech, Dec. 2009, Technical Data Sheet, 1 page.

\* cited by examiner

FOAMING MIXED ALCOHOL/WATER COMPOSITIONS COMPRISING A COMBINATION OF ALKYL SILOXANE AND A HYDROTROPE/SOLUBILIZER

CROSS-REFERENCE TO RELATED APPLICATIONS

This application claims priority under 35 U.S.C. § 119 to provisional application U.S. Ser. No. 62/705,590, filed Jul. 6, 2020, herein incorporated by reference in its entirety.

FIELD

The disclosure relates to foaming compositions and cleaning compositions and methods of use which employ synergistic combinations including a solubilizer and a non-surface-active alkyl siloxane for use in hand sanitization and detergent and rinse aid compositions. These foaming compositions have many benefits including the ease of formation of microemulsions in both water, alcohol/water solutions, and condensed hydrocarbons.

BACKGROUND

Certain foaming compositions may reduce the surface tension of a liquid by adsorbing at the liquid-gas interface. They may also reduce the interfacial tension between oil or alcohol and water by adsorbing at the liquid-liquid interface. These foaming compositions have a hydrophilic section that is attracted to water molecules and a hydrophobic section that repels water and simultaneously attaches itself to compounds made mostly of hydrocarbons. This reduction in surface tension allows the liquid to foam by making it more energetically favorable to create new surface.

These foaming compositions may be made up of a single compound, such as a surfactant, or two or more compound which interact with each other to provide the two necessary hydrophobic and hydrophilic regions, such as a silicone-based water insoluble compound and a hydrotrope. Certain liquids, like alcohols, have a very low surface tension and will not sufficiently dissolve surfactants due to their hydrophilic regions. Alcohols, for example, have only two main classes of compounds which may lower their surface tension sufficiently to allow foaming: silicone-based and fluoride-based surfactants.

Surfactants, because of their hydrophilic and hydrophobic regions, are often incorporated in a cleaning composition to clean soiled surfaces. One of the preferred mechanisms is by microemulsifying these soils. Surfactants are also often incorporated into an oil-in-water microemulsion to make oil containing products appear more homogenous. Examples of these oil containing products include cleaning products containing oily solvents for degreasing such as terpene and other water immiscible solvents. The surfactant systems generally employed in these cleaning products include a mixture of anionic or non-ionic surfactants and a short chain alcohol to help solubilize the oil phase and prevent liquid crystal formation. These surfactants may be replaced with two or more compounds which interact with each other to create the same microemulsions.

Due to the limited number of known agents which can foam these low surface tension liquids, availability may be limited. Therefore, there is a need to identify additional compounds that may be used to cause foaming in these low surface tension liquids.

SUMMARY

Applicant has identified a synergistic combination of non surface-active alkyl siloxanes and hydrotropes that act together to produce stable foam in mixtures of water and/or short chain alcohols. Neither compound works alone, yet together these compositions can form emulsions for hand and hard surface sanitization, cleaning compositions and soil removal. The combinations are effective in lowering the surface tension of water, alcohol/water solutions, and hydrocarbon condensates. Further, the foaming compositions are capable of forming emulsions with, and thus removing, oily and greasy stains. In an embodiment the foaming compositions can remove non-transfat and fatty acid stains. Generally, non-transfats are more difficult to remove than transfats both from a cleaning and removal standpoint as well as laundry safety concern due to heat of polymerization of the non-trans fats.

In an embodiment, the alkyl siloxanes must be linear include those of the general formula:

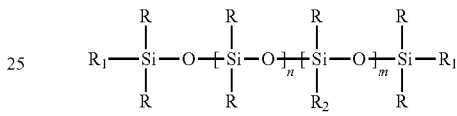

where
n is greater than or equal to 0,
m is greater than or equal to 0,
R and R1 are methyl
R2 is linear or branched, unsubstituted or substituted, saturated or unsaturated, aliphatic or aromatic C1-C30 hydrocarbon and cannot be a hydrophilic group.

In a preferred embodiment, R2 is a C2 to C28 hydrocarbon, n is 0 and m is 1.

In a more preferred embodiment R2 is a C2 to C12 hydrocarbon, n is 0 and m is 1.

In a most preferred embodiment R2 is a C8 hydrocarbon, n is 0 and m is 1.

The combination of alkyl siloxane and coupling agent together act as a surfactant and can be used in a number of traditional surfactant-based compositions such as cleaning compositions, rinse aides, pre-soaks, oily soil removal from energy systems and the like.

The hydrotrope is an ethoxylated castor oil, either hydrogenated or non hydrogenated. Importantly, other hydrotropes were tested in combination with the alkyl siloxane compounds and were not found to be effective and generating foaming or forming emulsions necessary for cleaning in water/short chain alcohol systems. These include PEG-400, B-cyclodextin, 1% Dioctyl Sulfosuccinate solution, lecithin, PEG(20) sorbitan monolaurate (Tween 20), PEG (80)sorbitan monolaurate (Tween 80), Sodium Coco PG-Dimonium Chloride Phosphate (Cola Lipid DCCA), Ethanol SDA-40B 190 proof (92.3% active), Castor Oil, N-Octyl-2-pyrrolidone, Surfadone LP-100, Isotridecyloxypropyl-1, 3-diaminopropane (Tomamine DA-17), C9-alcohol polyethylene glycol ether carboxylic acids (low foaming Marlowet 4539LF), Secondary Alcohol Ethoxylate (Tergitol 15-5-7), cocoamine oxide (Barlox-12 30%), SLES 60%, and Alcohol propoxysulfate (Alfoterra 123-85). In a preferred embodiment the composition does not contain one or more of these additional hydrdotropes.

In addition, the composition of akyl siloxane and hydrotrope were tested for foaming and emulsion forming ability with additional surfactants, and the inclusion of additional surfactants did not enhance performance. Additional surfactants which were tested include: PEG-40 Hydrogenated Castor Oil, PEG(20) sorbitan monolaurate (Tween 20), PEG(80) sorbitan monolaurate (Tween 80), PEG-400, Extended C10PO8E06, SLES (60%), cocoamine oxide (Barlox 12 (30%)), Caprylyl Methicone, PEG-40 Hydrogenated Castor Oil, t-Octylphenoxypolyethoxyethanol (Triton X-100), high foaming 50% active amine oxide (Tomamine AO-728), Lecithin, 1% citric acid, 1% Alkyl polyglucoside solution, Isotridecyloxypropyl-1,3-diaminopropane (Tomamine DA-17), Dicyclohexylamine and Polyoxyethylene-Polyoxypropylene Block Copolymer (Pluronic 68).

In an embodiment the castor oil has from about 20 moles to about 60 moles of PEG. The ratio of the two compositions needed is largely dependent on the amount of alcohol in the composition. For example, in a solution of 62% ethanol the siloxane can be as low as 0.2 wt. % to about 0.3% wt. %. The PEG modified castor oil can be as low as about 0.05 wt. % to about 0.07 wt. %. Surprisingly Applicants have demonstrated that the addition of surfactants to the mixture does not further help emulsion formation.

In preferred embodiments, ranges of alkyl pendant group length and siloxane backbone length, are mostly dictated by the solubility in the mixed ethanol/water systems, and C2 to C8 trisiloxane and ethyl methicone are most preferred.

In a further aspect of the present disclosure, a cleaning composition is provided which includes the foaming compositions with traditional additional components such as builders enzymes; and the like, the cleaning products being adapted to readily dissolve and disperse non trans fats in commercial, industrial and personal laundry washing processes or in a pre-spotting treatment.

These and other objects, features and attendant advantages of the present disclosure will become apparent to those skilled in the art from a reading of the following detailed description of the preferred embodiment and the appended claims.

DETAILED DESCRIPTION

Figure 1:
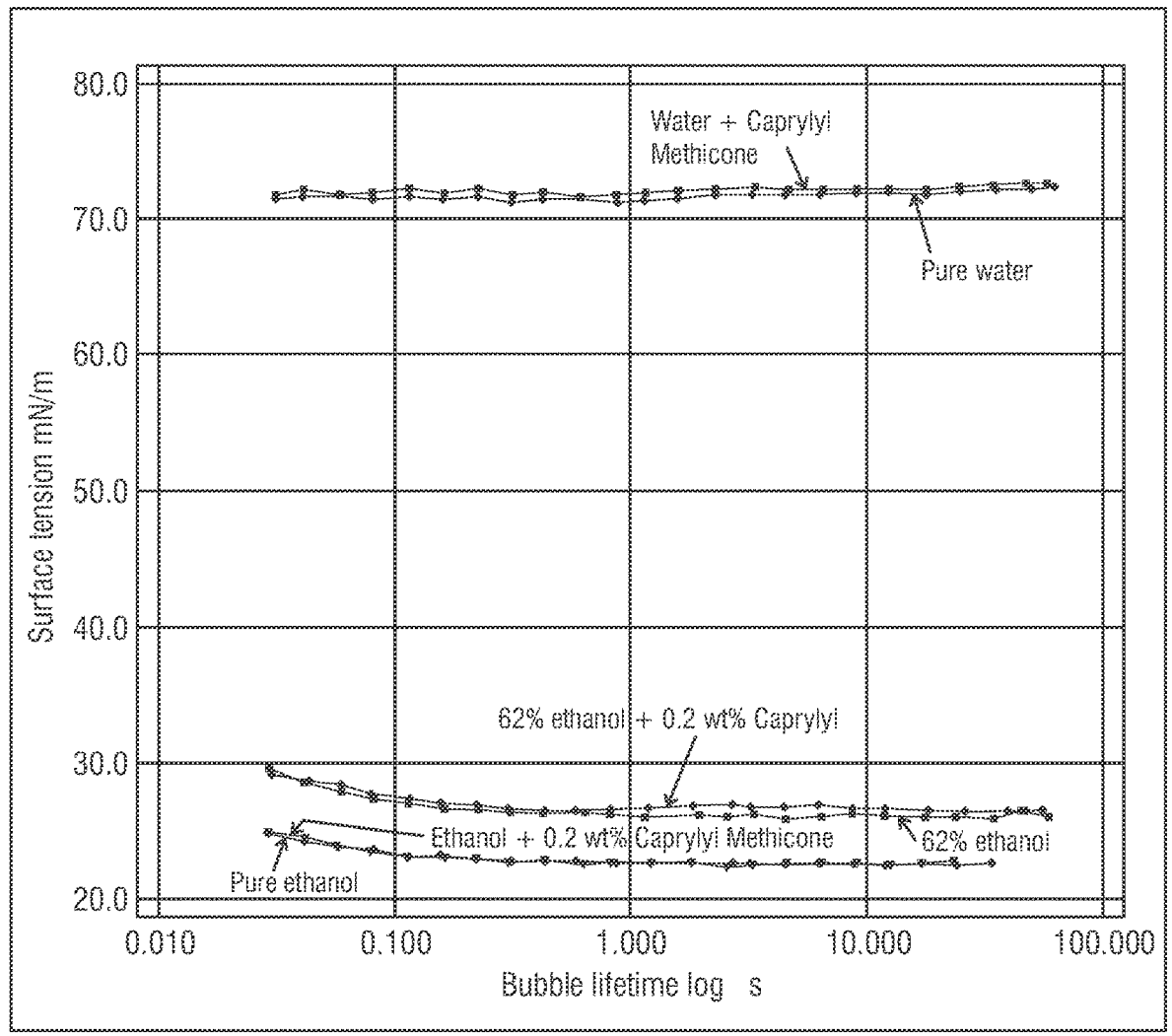
FIG. 1 shows a graphical representation of the results of a dynamic surface tension analysis indicating that caprylyl methicone has no surface activities on either water, ethanol, or 62 wt-% Ethanol SDA-40B 190 proof (92.3% active) interfaces.

The embodiments of this disclosure are not limited to particular applications of use for the inventive surfactant systems, which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

An "antiredeposition agent" refers to a compound that helps keep suspended in water instead of redepositing onto the object being cleaned. Antiredeposition agents are useful in the present disclosure to assist in reducing redepositing of the removed soil onto the surface being cleaned.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "cleaning composition" includes, unless otherwise indicated, detergent compositions, laundry cleaning compositions, hard surface cleaning compositions, including pretreatments or rinse aids, and personal care cleaning compositions for use in the health and beauty area. Cleaning compositions include granular, powder, liquid, gel, paste, bar form and/or flake type cleaning agents, laundry detergent cleaning agents, laundry soak or spray treatments, fabric treatment compositions, dish washing detergents and soaps, shampoos, body washes and soaps, and other similar cleaning compositions. As used herein, the term "fabric treatment composition" includes, unless otherwise indicated, fabric softening compositions, fabric enhancing compositions, fabric freshening compositions and combinations thereof. Such compositions may be, but need not be, rinse added compositions.

The term "electrolyte" refers to a substance that will provide ionic conductivity when dissolved in water or when in contact with it; such compounds may either be solid or liquid.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces, instruments and the like.

The term "soft surface" refers to a softer, highly flexible material such as fabric, carpet, hair, and skin.

The term "laundry" refers to items or articles that are cleaned in a laundry washing machine. In general, laundry refers to any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated.

Exemplary treated fibers include those treated for flame retardancy. It should be understood that the term "linen" is often used to describe certain types of laundry items including bed sheets, pillow cases, towels, table linen, table cloth, bar mops and uniforms. The disclosure additionally provides a composition and method for treating non-laundry articles and surfaces including hard surfaces such as dishes, glasses, and other wares.

As used herein, the term "microemulsion" refers to thermodynamically stable, isotropic dispersions consisting of nanometer size domains of water and/or oil stabilized by an interfacial film of surface-active agent characterized by ultra-low interfacial tension.

As used herein, the term "phosphate-free" refers to a composition, mixture, or ingredient that does not contain a phosphate or phosphate-containing compound or to which a phosphate or phosphate-containing compound has not been added. Should a phosphate or phosphate-containing compound be present through contamination of a phosphate-free composition, mixture, or ingredients, the amount of phosphate shall be less than 0.5 wt %. More preferably, the amount of phosphate is less than 0.1 wt %, and most preferably, the amount of phosphate is less than 0.01 wt %.

As used herein, the term "phosphorus-free" or "substantially phosphorus-free" refers to a composition, mixture, or ingredient that does not contain phosphorus or a phosphorus-containing compound or to which phosphorus or a phosphorus-containing compound has not been added. Should phosphorus or a phosphorus-containing compound be present through contamination of a phosphorus-free composition, mixture, or ingredients, the amount of phosphorus shall be less than 0.5 wt %. More preferably, the amount of phosphorus is less than 0.1 wt %, and most preferably the amount of phosphorus is less than 0.01 wt %.

As used herein, the term "polymer" generally includes, but is not limited to, homopolymers, copolymers, such as for example, block, graft, random and alternating copolymers, terpolymers, and higher "x"mers, further including their derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule.

"Soil" or "stain" refers to a non-polar oily substance which may or may not contain particulate matter such as mineral clays, sand, natural mineral matter, carbon black, graphite, kaolin, environmental dust, etc.

As used herein, the term "substantially free" refers to compositions completely lacking the component or having such a small amount of the component that the component does not affect the performance of the composition. The component may be present as an impurity or as a contaminant and shall be less than 0.5 wt %. In another embodiment, the amount of the component is less than 0.1 wt % and in yet another embodiment, the amount of component is less than 0.01 wt %.

The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both.

The term "surfactant" as used herein is a compound that contains a lipophilic segment and a hydrophilic segment, which when added to water or solvents, reduces the surface tension of the system. The lipophilic and hydrophilic segments of a surfactant are sufficiently large enough to cause spontaneous self-aggregation.

The term "hydrotrope" as used herein is a compound that solubilizes a hydrophobic compound in an aqueous solution. A hydrotrope generally has a hydrophilic region and a hydrophobic region that are too small to cause spontaneous self-aggregation. As such, hydrotropes, unlike surfactants, generally lack a critical micelle concentration or a critical vesicle concentration.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the disclosure include but are not limited to, those that include polypropylene polymers (PP), polycarbonate polymers (PC), melamine formaldehyde resins or melamine resin (melamine), acrilonitrile-butadiene-styrene polymers (ABS), and polysulfone polymers (PS). Other exemplary plastics that can be cleaned using the compounds and compositions of the disclosure include polyethylene terephthalate (PET) and polystyrene polyamide.

The term "weight percent," "wt.-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt.-%," etc.

The methods and compositions of the present disclosure may comprise, consist essentially of, or consist of the components and ingredients of the present disclosure as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Siloxane and Castor Oil Foaming Composition

The challenge to produce stable foam on 62 wt % ethanol solution interfaces is due to its already low surface tension (~25 mN/m2). Most surfactants, with the exceptions of silicone-based and fluoride-based surfactant) are incapable of reducing the water surface tension to such low value. The range of useful alkyl modified siloxane is limited by the ability of the hydrotrope system. When the length of the siloxane (PDMS) becomes too long, the hydrotrope no long can keep it in solution in the ethanol/water system. It has been discovered that a pendent alkyl siloxane and a PEG-modified castor oil may provide sufficient and stable foam to water, alcohol/water solutions, or hydrocarbon condensates. The pendent alkyl siloxanes lack a hydrophilic region. Without this region, the siloxanes are insoluble in an aqueous solution and cannot function as a silicone-based surfactant on their own.

Alkyl Siloxanes

In an embodiment, the alkyl siloxanes must be linear include those of the general formula:

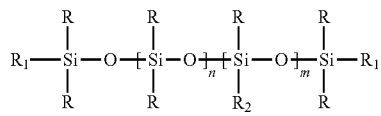

where
n is 0-30,
m is 1-50,
R and R1 are methyl
R2 is linear or branched, unsubstituted or substituted, saturated or unsaturated, aliphatic or aromatic C1-C30 hydrocarbon and cannot be a hydrophilic group.

In a preferred embodiment, R2 is a C2 to C28 hydrocarbon, and n is 0 to 30 and m is 1 to 50.

In a preferred embodiment, R2 is a C2 to C28 hydrocarbon, n is 0 and m is 1.

In a more preferred embodiment R2 is a C2 to C12 hydrocarbon, n is 0 and m is 1.

In a most preferred embodiment R2 is a C8 hydrocarbon, n is 0 and m is 1.

PEG Modified Castor Oil

The compositions of the invention may include one or more hydrotropes that aide in compositional stability and aqueous formulation. Functionally speaking, the suitable hydrotrope couplers which can be employed are non-toxic and retain the active ingredients in aqueous solution throughout the temperature range and concentration to which a concentrate or any use solution is exposed.

Any hydrotrope coupler may be used provided it does not react with the other components of the composition or negatively affect the performance properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters), amine oxides (mono-, di-, or tri-alkyl) and C8-C10 alkyl glucosides. Preferred coupling agents for use in the present invention include n-octanesulfonate, available as NAS 8D from Eco-lab Inc., n-octyl dimethylamine oxide, and the commonly available aromatic sulfonates such as the alkyl benzene sulfonates (e.g. xylene sulfonates) or naphthalene sulfonates, aryl or alkaryl phosphate esters or their alkoxylated analogues having 1 to about 40 ethylene, propylene or butylene oxide units or mixtures thereof. Other preferred hydrotropes include nonionic surfactants of C6-C24 alcohol alkoxylates (alkoxylate means ethoxylates, propoxylates, butoxylates, and co-or-terpolymer mixtures thereof) (preferably C6-C14 alcohol alkoxylates) having 1 to about 15 alkylene oxide groups (preferably about 4 to about 10 alkylene oxide groups); C6-C24 alkylphenol alkoxylates (preferably C8-C10 alkylphenol alkoxylates) having 1 to about 15 alkylene oxide groups (preferably about 4 to about 10 alkylene oxide groups); C6-C24 alkylpolyglycosides (preferably C6-C20 alkylpolyglycosides) having 1 to about 15 glycoside groups (preferably about 4 to about 10 glycoside groups); C6-C24 fatty acid ester ethoxylates, propoxylates or glycerides; and C4-C12 mono or dialkanolamides. A preferred hydrotrope is sodium xylenesulfonate (SXS).

In a preferred embodiment the hydrotrope is castor oil. Caster oil is a plant-derived oil obtained from the seeds (castor beans) of the plant *Ricinus communis*. It is a mixture of triglycerides composed of several different fatty acids. It is a mono-unsaturated fat, with a one double carbon-carbon bond per arm of the triglyceride. The major component is ricinoleic acid, with the remainder of the oil being comprised of oleic, linoleic, stearic, and several other organic acids.

The chemistry of the major component of ricinoleic acid is distinct among triglycerides. This fatty acid possesses hydroxyl (—OH) groups on each arm of the molecule, which make it more polar than other fatty acids. The hydroxyl group also facilitates chemical modification of the triglyceride, allowing creation of derivatives with desired properties for many different applications.

One such derivative, is PEG-x castor oil (x=number of ethylene glycol units). Ricinoleic acid (castor oil) reacted with ethylene oxide produces a polyethylene glycol modified castor oil, with the number of ethylene glycol units varying from as few as two to more than 100. The ethylene glycol portion of the molecule is hydrophilic (water soluble). This hydrophilic portion, coupled with the hydrophobic oil portion of the triglyceride, creates a nonionic surfactant molecule. These surfactant molecules can be used by formulators as excellent emulsifiers of conditioning agents, stabilizers, and thickeners. The ethylene glycol groups enhance the humectant properties of the castor oil molecule. PEG-castor oil molecules range from dispersible in aqueous solutions to completely water soluble, depending upon the PEG-#. When the PEG-# exceeds approximately 35, the molecule becomes completely water soluble.

The PEG modified castor oil for use in embodiments of the disclosure include those of the general formula:

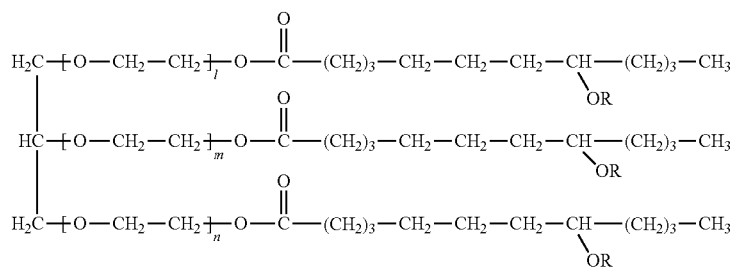

where l, m, and n are the average number of polyethylene glycol (PEG) units ranging from 1 to 100. Ion preferred embodiment the PEG modified castor oil includes 10 to 60 or more moles PEG preferable 20-60 moles.

Without being bound by a particular theory, it is believed that the hydrophobic R groups of the pendent alkyl siloxane both provide sufficient interaction with the hydrocarbons of the solution to improve its solubility and to interact with the hydrophobic tails of the PEG-modified castor oil. The PEG-modification of the castor oil then provides sufficient solubility for both compounds to be soluble in the solution. Due to this interaction, the two compounds act synergistically to allow for both sufficient solubility and to reduce surface tension sufficiently to make it energetically favorable to form foam. Therefore, due to this synergistic interaction, the two compounds combined may act as a surfactant in a number of solutions, including water, alcohol/water, and hydrocarbon condensates.

According to an embodiment, the foaming composition is employed in cleaning, rinsing, degreasing, and other formulations, and may replace the surfactant. The foaming compositions of the disclosure have been optimized to form stable microemulsions without the need for co-surfactants. Further, emulsions or microemulsions of different temperature range that are stable and irreversible, i.e. the emulsion or microemulsion does not revert as it stays in the specific temperature range may be created. The foaming composition of the disclosure is capable of forming emulsions or microemulsions with, or in cleaning compositions for removing or treated stains caused by oils and fatty acids including hydrocarbon type oils, vegetable oils, organic oils, mineral oils, synthetic oils, petrochemical oils, volatile essential oils, including fatty acids, lipids as well as triglycerides.

This feature may be used for removal of the oils in cleaning products or in any other product which requires an oil emulsion or microemulsion such as lubricants, suntan lotions, pharmaceutical applications hair products such as shampoos, gels, conditioners and the like, Petroleum products such as diesel fuel (petrodiesel), ethane (and other short-chain alkanes), fuel oils (heaviest of commercial fuels, used in ships/furnaces), gasoline (petrol), jet fuel, kerosene, and liquefied petroleum gas, lubrication products for various personal and engineering purposes, detergents, fertilizers, medicines, paints, plastics, synthetic fibers, and synthetic rubber.

The pendent alkyl siloxane may be present in the solution from about 0.01 wt % to about 10 wt %, from about 0.02 wt % to about 7 wt %, or from about 0.05 wt % to about 5 wt %.

Another angle is the successful formation of a microemulsion where the insoluble material is an alkyl methicone, and the hydrotrope is PEG modified castor oil, and the carrier/medium is a mixed ethanol. This microemulsion is highly different from most microemulsions as in most microemulsions, the insoluble component contributes to defoaming while the insoluble alkyl dimethicone in this special microemulsion contribute to foaming.

The compositions will also work with other short chain alcohols such as methanol and isopropanol. As such this disclosure may be very important for inhibition/prevention of methane hydrate blockage, as a preferred treatment is spraying a foam comprising short chain alcohols such as methanol.

Additionally, the there are other uses and applications which include but are not limited to laundry cleaning, reduction of laundry fire due to non-transfats, and hard surface cleaning such as manual pot-n-pan cleaning, machine warewashing, all-purpose cleaning, floor cleaning, CIP cleaning, open facility cleaning, foam cleaning, vehicle cleaning, etc. The disclosure is also relevant to non-cleaning related uses and applications such as dry lubes, tire dressings, polishes, etc. as well as triglyceride-based lotions, suntan lotions, potentially pharmaceutical emulsions, and microemulsions.

In certain embodiments the foaming composition is part of a cleaning composition which further traditional cleaning components such as a multiply charged cation such as Mg2+, Ca2+ or other functional electrolytes such as an alkalinity source or a chelating agent. The resultant combination is highly effective at forming microemulsions with non-transfats at relatively low temperatures. This system can be used in formulations for laundry detergents, hard surface cleaners, whether alkali or acid based, rinse aid, hard surface cleaner, even by itself as a pre-spotting agent, or other emulsion or microemulsion.

In such compositions the PEG modified castor oil may be present in the solution from about 0.05 wt % to about 10 wt %, from about 0.1 wt % to about 7 wt %, or from about 0.2 wt % to about 5 wt %.

Alcohol/Water Solutions Employing a Siloxane and Castor Oil Foaming Composition
Cleaning Composition Formulations In another embodiment the foaming compositions are formulated in cleaning compositions such as a ware wash or laundry detergent which include a builder, and other traditional components such as enzymes. Examples of such standard laundry, warewash components and formulations, which are well known to those skilled in the art, are provided in the following paragraphs.

The detergent or warewash composition can be provided in solid or liquid form and includes, for example, an alkalinity source, a metal protector (for warewash), a surfactant or surfactant system of the disclosure water, and a threshold agent, and other optional components. Typical formulations can include form about 30% and about 80% by weight alkalinity source, between about 15% and about 35% by weight metal protector, between about 2% and about 10% by weight surfactant, between about 0.1% and about 20% by weight water, between about 0.2% and about 15% by weight threshold agent. If a scale inhibitor is present it is present in an amount of from about 0 to about 15% by weight.

Yet another embodiment includes hard surface cleaning composition with the surfactant system of the disclosure, an acid source or source of alkalinity, and optionally a solvent, a water conditioning agent, and water to make a hard surface cleaner which will be effective at removing greasy and oily soils from surfaces such as showers, sinks, toilets, bathtubs, countertops, windows, mirrors, transportation vehicles, floors, and the like. These surfaces can be those typified as "hard surfaces" (such as walls, floors, bed-pans).

A typical hard surface formulation at about 18% activity includes between about 40 wt. % and about 80 wt. % surfactant system of the disclosure, between about 3 wt. % and about 18 wt. % water conditioning agent, between about 0.1 wt. % and about 0.55 wt. % acid or alkalinity source, between about 0 wt. % and about 10 wt. % solvent and between about 10 wt. % and about 60 wt. % water.

Particularly, the cleaning compositions include between about 45 wt. % and about 75 wt. % foaming system of the disclosure, between about 0 wt. % and about 10 wt. % optional co-surfactant, between about 5 wt. % and about 15 wt. % water conditioning agent, between about 0.3 wt. % and about 0.5 wt. % acid or alkalinity source, between about 0 and about 6 wt. % solvent and between about 15 wt. % and about 50 wt. % water. In other embodiments, similar intermediate concentrations and use concentrations may also be present in the cleaning compositions of the disclosure.

Additional traditional cleaning components.
Chelating Agent

The composition may optionally include a chelating agent. Examples of chelating agents include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. Other chelating agents include nitroloacetates and their derivatives, and mixtures thereof. Examples of aminocarboxylates include amino acetates and salts thereof. Suitable amino acetates include: N-hydroxyethylaminodiacetic acid; hydroxyethylenediaminetetraacetic acid; nitrilotriacetic acid (NTA); ethylenediaminetetraacetic acid (EDTA); Nhydroxyethyl-ethylenediaminetriacetic acid (HEDTA); tetrasodium ethylenediaminetetraacetic acid (EDTA); diethylenetriaminepentaacetic acid (DTPA); and alanine-N,N-diacetic acid; n-hydroxyethyliminodiacetic acid; and the like; their alkali metal salts; and mixtures thereof. Suitable aminophosphates include nitrilotrismethylene phosphates and other aminophosphates with alkyl or alkaline groups with less than 8 carbon atoms. Exemplary polycarboxylates iminodisuccinic acids (IDS), sodium polyacrylates, citric acid, gluconic acid, oxalic acid, salts thereof, mixtures thereof, and the like. Additional polycarboxylates include citric or citrate-type chelating agents, polymeric polycarboxylate, and acrylic or polyacrylic acid-type chelating agents. Additional chelating agents include polyaspartic acid or co-condensates of aspartic acid with other amino acids, C4-C25mono-or-dicarboxylic acids and C4-C25-mono-or-diamines. Exemplary polymeric polycarboxylates include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

The chelating agent may be present in an amount from about 0.01 to about 5 wt. %, from about 0.05 to about 3 wt. %, and from about 0.1 to about 1.5 wt. %.

Preservatives

The composition may optionally include a preservative. Generally, preservatives fall into specific classes including phenolics, halogen compounds, quaternary ammonium compounds, metal derivatives, amines, alkanolamines, nitro derivatives, biguanides, analides, organosulfur and sulfur-nitrogen compounds, alkyl parabens, and miscellaneous compounds. Some non-limiting examples of phenolic antimicrobial agents include pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof. Some non-limiting examples of halogen compounds include trichlorohydroxy diphenyl ether (Triclosan), sodium trichloroisocyanurate, sodium dichloroisocyanurate, iodine-poly(vinylpyrolidin-onen) complexes, and bromine compounds such as 2bromo-2-nitropropane-1,3-diol, and derivatives thereof. Some non-limiting examples of quaternary ammonium compounds include benzalkonium chloride, benzethonium chloride, behentrimonium chloride, cetrimonium chloride, and derivatives thereof. Some non-limiting examples of amines and nitro containing compounds include hexahydro-1,3,5-tris(2-hydroxyethyl)-s-triazine, dithiocarbamates such as sodium dimethyldithiocarbamate, and derivatives thereof. Some non-limiting examples of biguanides include polyaminopropyl biguanide and chlorhexidine gluconate. Some non-limiting examples of alkyl parabens include methyl, ethyl, propyl and butyl parabens. The preservative is preferably present in the composition in an amount from about 0 to about 3 wt. %, from about 0.1 to about 2 wt. %, and from about 0.2 to about 1 wt. %.

Thickener

The composition may optionally include a thickener. Exemplary thickeners include (1) cellulosic thickeners and their derivatives, (2) natural gums, (3) starches, (4) stearates, (5) fatty acid alcohols and (6) Polyethylene Oxide. Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of starches include oat flour, potato starch, wheat flour, wheat starch, and the like. Some non-limiting examples of stearates include PEG-150 distearate, methoxy PEG-22/dodecyl glycol copolymer, and the like. Some non-limiting examples of fatty acid alcohols include caprylic alcohol, cetearyl alcohol, lauryl alcohol, oleyl alcohol, palm kernel alcohol, and the like.

The amount of thickener in the composition depends on the desired viscosity of the composition. The composition preferably has a viscosity low enough to pump through a foamer such as an Airspray foamer and allow foaming.

Positively Charged Polymer

In certain embodiments the composition can include a protively charged polyerm for additional foam stabilization.

Positively Charged Polymer

According to the invention, the positively charged class of polymers such as polyethyleneimine (PEI) and its derivatives such as alkoxylated and/or ethoxylated (PEI) polymers, polyamines, polyquats, polyglycerol quats, and other PEI derivatives, their salts or mixtures may used in the compositions of the invention. PEI is a polymeric amine or a polyamine, and include, polyethyleneimine compounds (PEI) and/or its derivatives. Polyethyleneimines may include primary, secondary or tertiary amine compounds. The polyethyleneimine compounds and/or its derivatives may include linear and/or branched polyethyleneimines. Still further, polyethyleneimines and/or its derivatives can vary significantly in molecular weight, topology and shape, including for example linear, branched or comb-like structures as a result of ring-opening polymeriziation of the ethylenimine. See Angelescu et al., *Langmuir*, 27, 9961-9971 (2011), which is incorporated herein by reference in its entirety. According to an aspect of the invention, the bleach activator may be a linear and/or branched polyethyleneimine.

According to the invention, the positively charged class of polymers such as polyethyleneimine (PEI) and its derivatives such as ethoxylated (PEI) polymers, propoxylated (PEI) polymers, polyamines, polyquats, polyglycerol quats, and other PEI derivatives, their salts or mixtures thereof are used in foaming compositions to provide the electrostatic interaction with surfactants present in the foaming compositions, particularly preferred are ethoxylated or propoxylated PEI polymers. In preferred such embodiments, the PEI or PEIs are branched, spherical polymeric amines, and the molecular weight of the PEI or PEI salt used is from about 800 daltons to about 2 million Daltons. In addition, in preferred such embodiments, the charge density of the PEI or PEI salt used is from about 15 meq/g to about 25 meq/g, more preferably from about 16 meq/g to about 20 meq/g. Examples of such preferred PEIs include the BASF products LUPASOL WF (25 kDa; 16-20 meq/g) and Lupasol® FG (800 daltons; 16-20 meq/g), and the SOKALAN® family of polymers available from BASF, e.g., SOKALAN® HP20, SOKALAN® HP22 G, and the like.

According to the invention, cleaning compositions are formed with an detersive amount of an anionic surfactant (from about 1 wt. % to about 75 wt. %) and from about 0.01 wt. % to about 5.0 wt. % of ethoxylated PEI or other similarly positive charged polymer such as polyamines, polyquats, polyclycerol quats, and products commercially available from Nalco such as VX10035 a propoxylated PEI and two other Nalco products, VX9945 and VX9946, in which the PEI is first propoxylated then exthoxylated. Linear polyethyleneimines are made by the cationic polymerization of oxazoline and oxazine derivatives. Methods for preparing linear PEIs are more fully described in Advances in Polymer Science, Vol. 102, pgs. 171-188, 1992 (references 6-31) which is incorporated in its entirety herein by reference. Polyethyleneimines can also be made by the polymerization of aziridine to afford a polymeric amine often containing primary, secondary, and tertiary amine functionality. Commercial preparation of PEIs are generally acid-catalyzed reactions to open the ring of ethyleneimine, also known as aziridine as shown below.

Suitable polyethyleneimine compounds useful in the present invention may contain a mixture of primary, secondary, and tertiary amine substituents. The mixture of primary, secondary, and tertiary amine substituents may be in any ratio, including for example in the ratio of about 1:1:1 to about 1:2:1 with branching every 3 to 3.5 nitrogen atoms along a chain segment. Alternatively, suitable polyethyleneimine compounds may be primarily one of primary, secondary or tertiary amine substituents.

Exemplary PEI products include multifunctional cationic polyethyleneimines with branched polymer structures according to the following formulas $(-(CH_2-CH_2-NH)_n-)$, with a molecular mass of 43.07 (as repeating units). In certain aspects the formula $(-(CH_2-CH_2-NH)_n-)$ has a value of n that is at least 10 to $10^5$, and wherein the nitrogen to carbon ratio is 1:2. PEI polymers have the general following polymer structure:

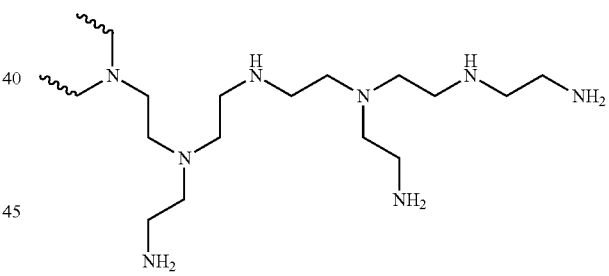

PEI products can also be represented by the following general formula, which may vary according to substitutions, size, molecular weight, branching, and the like:

wherein x is an integer that is 1 or greater and y is an integer that is 1 or greater than 1. Preferably, wherein x is an integer from about 1 to about 120,000, preferably from about 2 to about 60,000, more preferably from about 3 to about 24,000 and y is an integer from about 1 to about 60,000, preferably from about 2 to about 30,000, more preferably from about 3 to about 12,000.

Various commercial polyethyleneimines are available, including for example those sold under the tradename Lupasol® (BASF), including for example Lupasol® FG, Lupasol® G, Lupasol® PR 8515, Lupasol® WF, Lupasol® G20/35/100, Lupasol® HF, Lupasol® P, Lupasol® PS, Lupasol® PO 100, Lupasol® PN 50/60, and Lupasol® SK. Such exemplary polyethyleneimines are available as anhydrous polyethyleneimines and/or modified polyethyleneimines provided in aqueous solutions or methoyxypropanol (Lupasol® PO 100). The molar mass of the polyethyleneimines, including modified polyethyleneimines can vary from about 800 g/mol to at least 2,000,000 g/mol.

In certain aspects the polymeric amine bleach activators, and preferably the PEI bleach activators, may be a branched, spherical polymeric amine. In further aspects, the molecular weight of the polymeric amine bleach activators or PEI bleach is from about 100 Daltons to about 2 million Daltons (PEI-2,000,000), more preferably from about 100 Daltons to about 1 million Daltons (PEI-1,000,000), more preferably from about 500 Daltons to about 500 kDa (PEI-500,000), more preferably from about 500 Daltons to about 50 kDa (PEI-50,000), more preferably from about 800 Daltons to about 50 kDa (PEI-50,000), more preferably from about 800 Daltons to about 10 kDa (PEI-10,000). In further aspects, the charge density of the PEI or PEI salt is from about 15 meq/g to about 25 meq/g, more preferably from about 16 meq/g to about 20 meq/g. Commercially-available examples of such preferred PEIs include the BASF products LUPASOL☐ WF (25 kDa; 16-20 meq/g) and Lupasol☐ FG (800 Daltons; 16-20 meq/g), and the BASF products in the SOKALAN☐ family of polymers, e.g., SOKALAN☐ HP20, SOKA-LAN☐ HP22 G, and the like.

In an aspect, a polymeric amine may contain other substituents and/or and copolymers. For example, a polymeric amine may also include substituents, including for example ethoxylates and propoxylates. In an aspect of the invention, the polymeric amine, such as a polyethyleneimines, are derivatized with ethylene oxide (EO) and/or propylene oxide (PO) side chains. According to the invention, the PEI does not contain propylene oxide side chains. In an exemplary aspect of the invention ethoxylated PEIs may be heavily branched, wherein the substitutable hydrogens on the primary and secondary nitrogens are replaced with ethoxylated chains containing varying degrees of repeating units, such as the following polymer structure (generic for PEI20EO):

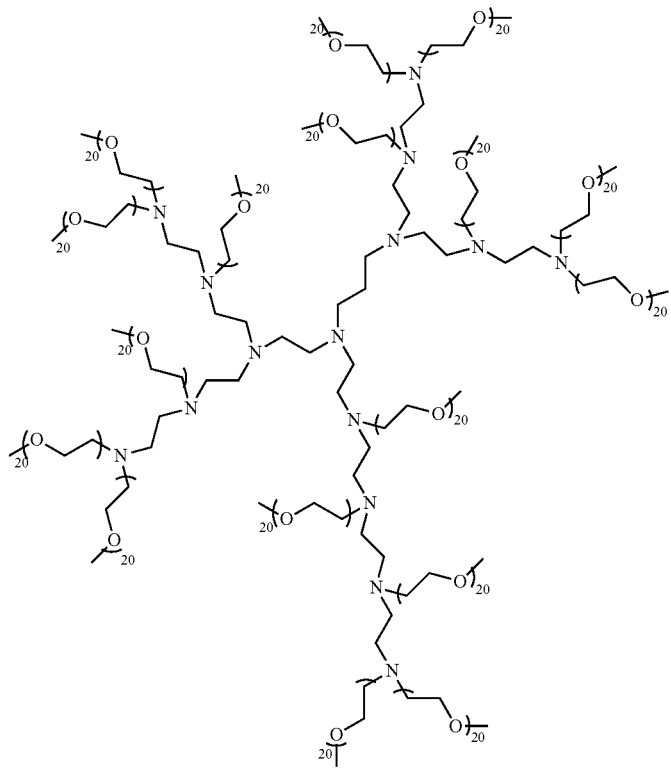

In an aspect, the positively charged polymer is a polyethyleneimine polymer with ethyleneoxide chains. Ethoxylation of PEIs increases the solubility of the bleach activator according to the invention.

A polymeric amine may also include copolymers, including for example ethylenediamine. A variety of substituents and/or copolymers may be included in order to modify the solubility or any other physical characteristics of a particular polymeric amine employed as a bleach activator according to the invention.

Because of the presence of amine groups, PEI can be protonated with acids to form a PEI salt from the surrounding medium resulting in a product that is partially or fully ionized depending on pH. For example, about 73% of PEI is protonated at pH 2, about 50% of PEI is protonated at pH 4, about 33% of PEI is protonated at pH 5, about 25% of PEI is protonated at pH 8 and about 4% of PEI is protonated at pH 10. In general, PEIs can be purchased as their protonated or unprotonated form with and without water. An example of a segment of a branched protonated polyethyleneimine (PEI salt) is shown below:

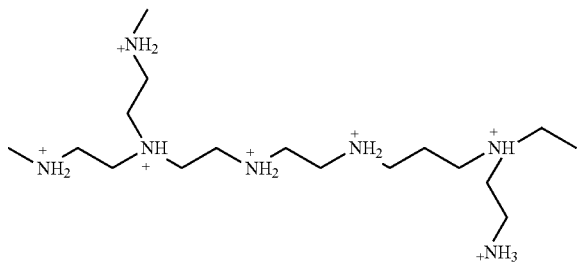 [SMILES: CCN(CC[NH3+])CCCNCCNCCN(CCNC)CC[NH2+]C]

The counterion of each protonated nitrogen center is balanced with an anion of an acid obtained during neutralization. Examples of protonated PEI salts include, but are not limited to, PEI-hydrochloride salt, PEI-sulfuric acid salt, PEI-nitric acid salt, PEI-acetic acid salt PEI fatty acid salt and the like. In fact, any acid can be used to protonate PEIs resulting in the formation of the corresponding PEI salt compound.

The cationic polymer, PEI is present in an amount of from about 0.01 wt. % 1 to about 5 wt. %. At greater than 5 wt % the affect is decreased and this is a critical upper limit.

Cleaning Compositions

The foaming compositions of the disclosure may replace the surfactants found in cleaning compositions due to the synergistic hydrophilic region on the PEG-modified castor oil and a hydrophobic region on both the alkyl siloxane and the PEG-modified castor oil. The foaming compositions of the disclosure may be used alone, as a pre-spot or pre-treatment composition in combination with a traditional detergent or cleaner or may be incorporated within a cleaning composition. The disclosure comprises both hard surface and soft surface cleaning compositions employing the disclosed surfactant system.

In one embodiment, the disclosure employs the foaming compositions of the disclosure, an acid source, a solvent, a water conditioning agent, and water to make a hard surface cleaner which will be effective at removing greasy and oily soils from surfaces such as showers, sinks, toilets, bathtubs, countertops, windows, mirrors, transportation vehicles, floors, and the like. These surfaces can be those typified as "hard surfaces" (such as walls, floors, bed-pans).

A typical hard surface formulation at about 18% activity includes between about 40 wt. % and about 80 wt. % foaming compositions of the disclosure, between about 3 wt. % and about 18 wt. % water conditioning agent, between about 0.1 wt. % and about 0.55 wt. % acid source, between about 0 wt % and about 10 wt. % solvent and between about 10 wt. % and about 60 wt. % water.

Particularly, the cleaning compositions include between about 45 wt. % and about 75 wt. % foaming compositions of the disclosure, between about 0 wt. % and about 10 wt. % optional co-surfactant, between about 5 wt. % and about 15 wt. % water conditioning agent, between about 0.3 wt. % and about 0.5 wt. % acid source, between about 0 and about 6 wt. % solvent and between about 15 wt. % and about 50 wt. % water. In other embodiments, similar intermediate concentrations and use concentrations may also be present in the cleaning compositions of the disclosure.

In a laundry detergent formulation, the compositions of the disclosure typically include the foaming compositions of the disclosure, and a builder, optionally with an enzyme. Examples of such standard laundry detergent ingredients, which are well known to those skilled in the art, are provided in the following paragraphs.

While not essential for the purposes of the present disclosure, the non-limiting list of additional components illustrated hereinafter are suitable for use in the instant compositions and may be desirably incorporated in certain embodiments of the disclosure, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable additional materials include, but are not limited to, surfactants, builders, chelating agents, dye transfer inhibiting agents, viscosity modifiers, dispersants, additional enzymes, and enzyme stabilizers, catalytic materials, bleaches, bleach activators, hydrogen peroxide, sources of hydrogen peroxide, preformed peracids, polymeric dispersing agents, threshold inhibitors for hard water precipitation pigments, clay soil removal/anti-redeposition agents, brighteners, suds suppressors, dyes, fabric hueing agents, perfumes, structure elasticizing agents, fabric softeners, carriers, additional hydrotropes, processing aids, solvents, pigments antimicrobials, pH buffers, processing aids, active fluorescent whitening ingredient, additional surfactants and mixtures thereof. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' compositions. Thus, certain embodiments of Applicants' compositions do not contain additional materials. However, when one or more additional materials are present, such one or more additional components may be present as detailed below:

The liquid detergent herein has a neat pH of from about 7 to about 13, or about 7 to about 9, or from about 7.2 to about 8.5, or from about 7.4 to about 8.2. The detergent may contain a buffer and/or a pH-adjusting agent, including inorganic and/or organic alkalinity sources and acidifying agents such as water-soluble alkali metal, and/or alkali earth metal salts of hydroxides, oxides, carbonates, bicarbonates, borates, silicates, phosphates, and/or metasilicates; or sodium hydroxide, potassium hydroxide, pyrophosphate, orthophosphate, polyphosphate, and/or phosphonate. The organic alkalinity source herein includes a primary, secondary, and/or tertiary amine. The inorganic acidifying agent herein includes HF, HCl, HBr, HI, boric acid, sulfuric acid, phosphoric acid, and/or sulphonic acid; or boric acid. The organic acidifying agent herein includes substituted and substituted, branched, linear and/or cyclic $C_{1-30}$ carboxylic acid.

Bleaching Agents

The cleaning compositions of the present disclosure may comprise one or more bleaching agents. Suitable bleaching agents other than bleaching catalysts include photobleaches, bleach activators, hydrogen peroxide, sources of hydrogen peroxide, preformed peracids and mixtures thereof. In general, when a bleaching agent is used, the compositions of the present disclosure may comprise from about 0.1% to about 50% or even from about 0.1% to about 25% bleaching agent by weight of the subject cleaning composition. Examples of suitable bleaching agents include:

(1) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxzone®, and mixtures thereof. Suitable percarboxylic acids include hydrophobic and hydrophilic peracids having the formula R—(C—O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen; (2) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the disclosure the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (3) bleach activators having R—(C—O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the disclosure the subject cleaning composition may comprise NOBS, TAED or mixtures thereof.

When present, the peracid and/or bleach activator is generally present in the composition in an amount of from about 0.1 to about 60 wt %, from about 0.5 to about 40 wt or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Additional Surfactant

In some embodiments, the compositions may include an additional surfactant. Additional surfactants can be anionic, nonionic, cationic zwitterionic and can also include additional extended chain surfactants as discussed herein.

The cleaning composition can contain an additional anionic surfactant component that includes a detersive amount of an anionic surfactant or a mixture of anionic surfactants. Anionic surfactants are desirable in cleaning compositions because of their wetting and detersive properties. The anionic surfactants that can be used according to the disclosure include any anionic surfactant available in the cleaning industry. Suitable groups of anionic surfactants include sulfonates and sulfates. Suitable surfactants that can be provided in the anionic surfactant component include alkyl aryl sulfonates, secondary alkane sulfonates, alkyl methyl ester sulfonates, alpha olefin sulfonates, alkyl ether sulfates, alkyl sulfates, and alcohol sulfates.

Suitable alkyl aryl sulfonates that can be used in the cleaning composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate.

Suitable alkane sulfonates that can be used in the cleaning composition can have an alkane group having 6 to 24 carbon atoms. Suitable alkane sulfonates that can be used include secondary alkane sulfonates. A suitable secondary alkane sulfonate includes sodium $C_{14}$-$C_{17}$ secondary alkyl sulfonate commercially available as Hostapur SAS from Clariant.

Suitable alkyl methyl ester sulfonates that can be used in the cleaning composition include those having an alkyl group containing 6 to 24 carbon atoms. Suitable alpha olefin sulfonates that can be used in the cleaning composition include those having alpha olefin groups containing 6 to 24 carbon atoms.

Suitable alkyl ether sulfates that can be used in the cleaning composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether sulfate and is available under the name Steol CS-460.

Suitable alkyl sulfates that can be used in the cleaning composition include those having an alkyl group containing 6 to 24 carbon atoms. Suitable alkyl sulfates include, but are not limited to, sodium lauryl sulfate and sodium lauryl/myristyl sulfate.

Suitable alcohol sulfates that can be used in the cleaning composition include those having an alcohol group containing about 6 to about 24 carbon atoms.

The anionic surfactant can be neutralized with an alkaline metal salt, an amine, or a mixture thereof. Suitable alkaline metal salts include sodium, potassium, and magnesium. Suitable amines include monoethanolamine, triethanolamine, and monoisopropanolamine. If a mixture of salts is used, a suitable mixture of alkaline metal salt can be sodium and magnesium, and the molar ratio of sodium to magnesium can be between about 3:1 and about 1:1.

The cleaning composition, when provided as a concentrate, can include the additional anionic surfactant component in an amount sufficient to provide a use composition having desired wetting and detersive properties after dilution with water. The concentrate can contain about 0.1 wt. % to about 0.5 wt. %, about 0.1 wt. % to about 1.0 wt. %, about 1.0 wt. % to about 5 wt. %, about 5 wt. % to about 10 wt. %, about 10 wt. % to about 20 wt. %, 30 wt. %, about 0.5 wt. % to about 25 wt. %, and about 1 wt. % to about 15 wt. %, and similar intermediate concentrations of the anionic surfactant.

The cleaning composition can contain a nonionic surfactant component that includes a detersive amount of nonionic surfactant or a mixture of nonionic surfactants. Nonionic surfactants can be included in the cleaning composition to enhance grease removal properties. Although the surfactant component can include a nonionic surfactant component, it should be understood that the nonionic surfactant component can be excluded from the detergent composition.

Additional nonionic surfactants that can be used in the composition include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants include a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt %.

Other nonionic surfactants include alcohol alkoxylates. A suitable alcohol alkoxylate include linear alcohol ethoxylates such as Tomadol™ 1-5 which is a surfactant containing an alkyl group having 11 carbon atoms and 5 moles of ethylene oxide. Additional alcohol alkoxylates include alkylphenol ethoxylates, branched alcohol ethoxylates, secondary alcohol ethoxylates (e.g., Tergitol 15-S-7 from Dow Chemical), castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauric diethanolamide, polyethylene glycol cocoamide (e.g., PEG-6 cocoamide), oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglucosides, or mixtures thereof.

When nonionic surfactants are included in the detergent composition concentrate, they can be included in an amount of at least about 0.1 wt. % and can be included in an amount of up to about 15 wt. %. The concentrate can include about 0.1 to 1.0 wt. %, about 0.5 wt. % to about 12 wt. % or about 2 wt. % to about 10 wt. % of the nonionic surfactant.

Amphoteric surfactants can also be used to provide desired detersive properties. Suitable amphoteric surfactants that can be used include, but are not limited to betaines, imidazolines, and propionates. Suitable amphoteric surfactants include, but are not limited to: sultaines, amphopropionates, amphodipropionates, aminopropionates, aminodipropionates, amphoacetates, amphodiacetates, and amphohydroxypropylsulfonates.

When the detergent composition includes an amphoteric surfactant, the amphoteric surfactant can be included in an amount of about 0.1 wt % to about 15 wt %. The concentrate can include about 0.1 wt % to about 1.0 wt %, 0.5 wt % to about 12 wt % or about 2 wt % to about 10 wt % of the amphoteric surfactant.

The cleaning composition can contain a cationic surfactant component that includes a detersive amount of cationic surfactant or a mixture of cationic surfactants. Cationic co-surfactants that can be used in the cleaning composition include, but are not limited to: amines such as primary, secondary and tertiary monoamines with C18 alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and quaternary ammonium salts, as for example, alkylquaternary ammonium chloride surfactants such as n-alkyl($C_{12}$-$C_{18}$)dimethylbenzyl ammonium chloride, n-tetradecyldimethylbenzylammonium chloride monohydrate, and a naphthylene-substituted quaternary ammonium chloride such as dimethyl-1-naphthylmethylammonium chloride.

In some embodiments the additional surfactant may be an extended surfactant. Extended surfactants include a linker polyalkylene glycol link.

The general formula for a nonionic extended surfactant is $$R\text{-}[L]_x\text{-}[O\text{—}CH_2\text{—}CH_2]_y$$

where R is the lipophilic moiety, such as a linear or branched, saturated or unsaturated, substituted or unsubstituted, aliphatic or aromatic hydrocarbon radical having from about 8 to 20 carbon atoms, L is a linking group, such as a block of poly-alkylene oxide, preferably polypropylene oxide; x is the chain length of the linking group ranging from 2-25; and y is the average degree of ethoxylation ranging from 1-18. In a preferred embodiment, applicants have found that use of a nonionic surfactant with enough PO extension as the main surfactant (and only) can form liquid single phase microemulsions. PO length is optimized at from about 5 to about 8 moles of PO. This length of PO extension provides a lower foam profile. Applicants have further found that R groups that are a branched hydrophobe such as a guerbet alcohol are better for protein soil defoaming.

Preferred extended surfactants include: branched Guerbet alcohol alkoxylates; such as $C_y(PO)_8(EO)_x$ (x=3, 6, 8, 10) (y=10-12) also, extended linear alcohol alkoxylates; $C_{(12-14)}(PO)_{16}(EO)_x$ (x=6, 12, 17).

Branched Alcohol Alkoxylates

Preferred branched alcohol alkoxylates include Guerbet ethoxylates. Guerbet ethoxylates suitable for use herein have the following formula:

$$CH_3(CH_2)_n\underset{R^1}{C}HCH_2O(CH_2\underset{R^2}{C}HO)_mH$$

In an embodiment the Guerbet ethoxylate is further defined wherein $R^1$ is C2-C20 alkyl and $R^2$ is H or C1-C4 alkyl. In a further embodiment, the Guerbet ethoxylate is defined wherein "n" is an integer between 2 and 20 and wherein "m" is an integer between 1 and 40.

In another embodiment, the branched alcohol alkoxylate is a Guerbet ethoxylate that is prepared from a Guerbet alcohol by dimerization of alkenes (e.g. butane).

The branched alcohol alkoxylates, including Guerbet ethoxylates, can be prepared according to U.S. Pat. Nos. 6,906,320, 6,737,553 and 5,977,048, the disclosure of these patents are herein incorporated by reference in their entirety. Exemplary branched alcohol alkoxylates include those available under the tradenames Lutensol XP-30 and Lutensol XP-50 (BASF Corporation). In general, Lutensol XP-30 can be considered to have 3 repeating ethoxy groups, and Lutensol XP-50 can be considered to have 5 repeating ethoxy groups.

Branched alcohol alkoxylates can be classified as relatively water insoluble or relatively water soluble. In general, a water insoluble branched alcohol alkoxylate can be considered an alkoxylate that, when provided as a composition containing 5 wt.-% of the branched alcohol alkoxylate and 95 wt.-% water, has a tendency to phase separate. Lutensol XP-30 and Lutensol XP-50 from BASF Corporation are examples of water-insoluble branched alcohol alkoxylates.

According to an embodiment, a branched alcohol alkoxylate, preferably a water-insoluble Guerbet ethoxylate has from about 10 wt.-% to about 90 wt.-% ethylene oxide, from about 20 wt.-% to about 70 wt.-% ethylene oxide preferably from about 30 wt.-% to about 60 wt.-% ethylene oxide.

Applicants have further found that use of capped extended nonionic surfactants lowers the foam profile of the composition and foam from protein soil.

Capped extended nonionic surfactants can include:

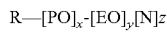

Where N is a capping group such as an alkyl group such as methyl, benzyl, butyl, etc.; a PO group of from 1-5 length, in length. These capped nonionic surfactants have lowered foam profiles and the like are effective for rinse aid formulations and detergents.

Builders

The cleaning compositions of the present disclosure may comprise one or more detergent builders or builder systems. When a builder is used, the subject composition will typically comprise at least about 1%, from about 5% to about 60% or even from about 10% to about 40% builder by weight of the subject composition. The detergent may contain an inorganic or organic detergent builder which counteracts the effects of calcium, or other ion, water hardness. Examples include the alkali metal citrates, succinates, malonates, carboxymethyl succinates, carboxylates, polycarboxylates and polyacetyl carboxylate; or sodium, potassium and lithium salts of oxydisuccinic acid, mellitic acid, benzene polycarboxylic acids, and citric acid; or citric acid and citrate salts. Organic phosphonate type sequestering agents such as DEQUEST® by Monsanto and alkanehydroxy phosphonates are useful. Other organic builders include higher molecular weight polymers and copolymers, e.g., polyacrylic acid, polymaleic acid, and polyacrylic/polymaleic acid copolymers and their salts, such as SOKALAN® by BASF. Generally, the builder may be up to 30%, or from about 1% to about 20%, or from about 3% to about 10%.

The compositions may also contain from about 0.01% to about 10%, or from about 2% to about 7%, or from about 3% to about 5% of a $C_{8-20}$ fatty acid as a builder. The fatty acid can also contain from about 1 to about 10 EO units. Suitable fatty acids are saturated and/or unsaturated and can be obtained from natural sources such a plant or animal esters (e.g., palm kernel oil, palm oil, coconut oil, babassu oil, safflower oil, tall oil, tallow and fish oils, grease, and mixtures thereof), or synthetically prepared (e.g., via the oxidation of petroleum or by hydrogenation of carbon monoxide via the Fisher Tropsch process). Useful fatty acids are saturated $C_{12}$ fatty acid, saturated $C_{12-14}$ fatty acids, saturated or unsaturated $C_{12-18}$ fatty acids, and a mixture thereof. Examples of suitable saturated fatty acids include captic, lauric, myristic, palmitic, stearic, arachidic and behenic acid. Suitable unsaturated fatty acids include: palmitoleic, oleic, linoleic, linolenic and ricinoleic acid.

Dye Transfer Inhibiting Agents

The cleaning compositions of the present disclosure may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Optical Brightener

In some embodiments, an optical brightener component, may be present in the compositions of the present disclosure. The optical brightener can include any brightener that is capable of eliminating graying and yellowing of fabrics. Typically, these substances attach to the fibers and bring about a brightening and simulated bleaching action by converting invisible ultraviolet radiation into visible longer-wave length light, the ultraviolet light absorbed from sunlight being irradiated as a pale bluish fluorescence and, together with the yellow shade of the grayed or yellowed laundry, producing pure white.

Fluorescent compounds belonging to the optical brightener family are typically aromatic or aromatic heterocyclic materials often containing condensed ring systems. An important feature of these compounds is the presence of an uninterrupted chain of conjugated double bonds associated with an aromatic ring. The number of such conjugated double bonds is dependent on substituents as well as the planarity of the fluorescent part of the molecule. Most brightener compounds are derivatives of stilbene or 4,4'-diamino stilbene, biphenyl, five membered heterocycles (triazoles, oxazoles, imidazoles, etc.) or six membered heterocycles (cumarins, naphthalamides, triazines, etc.).

Optical brighteners useful in the present disclosure are known and commercially available. Commercial optical brighteners which may be useful in the present disclosure can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles and other miscellaneous agents. Examples of these types of brighteners are disclosed in "The Production and Application of Fluorescent Brightening Agents", M. Zahradnik, Published by John Wiley & Sons, New York (1982), the disclosure of which is incorporated herein by reference.

Stilbene derivatives which may be useful in the present disclosure include, but are not necessarily limited to, derivatives of bis(triazinyl)amino-stilbene; bisacylamino derivatives of stilbene; triazole derivatives of stilbene; oxadiazole derivatives of stilbene; oxazole derivatives of stilbene; and styryl derivatives of stilbene. In an embodiment, optical brighteners include stilbene derivatives.

In some embodiments, the optical brightener includes Tinopal UNPA, which is commercially available through the Ciba Geigy Corporation located in Switzerland.

Additional optical brighteners for use in the present disclosure include, but are not limited to, the classes of substance of 4,4'-diamino-2,2'-stilbenedisulfonic acids (flavonic acids), 4,4'-distyrylbiphenyls, methylumbelliferones, coumarins, dihydroquinolinones, 1,3-diarylpyrazolines, naphthalimides, benzoxazol, benzisoxazol and benzimidazol systems, and pyrene derivatives substituted by heterocycles, and the like. Suitable optical brightener levels include lower levels of from about 0.01, from about 0.05, from about 0.1 or even from about 0.2 wt % to upper levels of 0.5 or even 0.75 wt %.

Dispersants

The compositions of the present disclosure can also contain dispersants. Suitable water-soluble organic materials include the homo- or co-polymeric acids or their salts, in which the polycarboxylic acid comprises at least two carboxyl radicals separated from each other by not more than two carbon atoms.

Enzymes

The cleaning compositions can comprise one or more enzymes which provide cleaning performance and/or fabric care benefits. Enzymes can be included herein for a wide variety of fabric laundering purposes, including removal of protein-based, carbohydrate-based, or triglyceride-based stains, for example, and/or for fabric restoration. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, amylases, or combinations thereof and may be of any suitable origin. The choice of enzyme(s) takes into account factors such as pH-activity, stability optima, thermostability, stability versus active detergents, chelants, builders, etc. A detersive enzyme mixture useful herein is a protease, lipase, cutinase and/or cellulase in conjunction with amylase. Sample detersive enzymes are described in U.S. Pat. No. 6,579,839.

Enzymes are normally present at up to about 5 mg, more typically from about 0.01 mg to about 3 mg by weight of active enzyme per gram of the detergent. Stated another way, the detergent herein will typically contain from about 0.001% to about 5%, or from about 0.01% to about 2%, or from about 0.05% to about 1% by weight of a commercial enzyme preparation. Protease enzymes are present at from about 0.005 to about 0.1 AU of activity per gram of detergent. Proteases useful herein include those like subtilisins from *Bacillus* [e.g. *subtilis, lentus, licheniformis, amyloliquefaciens* (BPN, BPN'), *alcalophilus*,] e.g. Esperase®, Alcalase®, Everlase® and Savinase® (Novozymes), BLAP and variants (Henkel). Further proteases are described in EP 130756, WO 91/06637, WO 95/10591 and WO 99/20726.

Amylases are described in GB Pat. #1 296 839, WO 94/02597 and WO 96/23873; and available as Purafect Ox Am® (Genencor), Termamyl®, Natalase®, Ban®, Fungamyl®, Duramyl® (all Novozymes), and RAPIDASE (International Bio-Synthetics, Inc).

The cellulase herein includes bacterial and/or fungal cellulases with a pH optimum between 5 and 9.5. Suitable cellulases are disclosed in U.S. Pat. No. 4,435,307 to Barbesgoard, et al., issued Mar. 6, 1984. Cellulases useful herein include bacterial or fungal cellulases, e.g. produced by *Humicola insolens*, particularly DSM 1800, e.g. 50 kD and ~43 kD (Carezyyme®). Additional suitable cellulases are the EGIII cellulases from *Trichoderma longibrachiatum*. WO 02/099091 by Novozymes describes an enzyme exhibiting endo-beta-glucanase activity (EC 3.2.1.4) endogenous to *Bacillus* sp., DSM 12648; for use in detergent and textile applications; and an anti-redeposition endo-glucanase in WO 04/053039. Kao's EP 265 832 describes alkaline cellulase K, CMCase I and CMCase II isolated from a culture product of *Bacillus* sp KSM-635. Kao further describes in EP 1 350 843 (KSM S237; 1139; KSM 64; KSM N131), EP 265 832A (KSM 635, FERM BP 1485) and EP 0 271 044 A (KSM 534, FERM BP 1508; KSM 539, FERM BP 1509; KSM 577, FERM BP 1510; KSM 521, FERM BP 1507; KSM 580, FERM BP 1511; KSM 588, FERM BP 1513; KSM 597, FERM BP 1514; KSM 522, FERM BP 1512; KSM 3445, FERM BP 1506; KSM 425. FERM BP 1505) readily-mass producible and high activity alkaline cellulases/endo-glucanases for an alkaline environment. Such endo-glucanase may contain a polypeptide (or variant thereof) endogenous to one of the above *Bacillus* species. Other suitable cellulases are Family 44 Glycosyl Hydrolase enzymes exhibiting endo-beta-1,4-glucanase activity from *Paenibacilus polyxyma* (wild-type) such as XYG1006 described in WO 01/062903 or variants thereof. Carbohydrases useful herein include e.g. mannanase (see, e.g., U.S. Pat. No. 6,060,299), pectate lyase (see, e.g., WO99/27083), cyclomaltodextrin glucanotransferase (see, e.g., WO96/33267), and/or xyloglucanase (see, e.g., WO99/02663). Bleaching enzymes useful herein with enhancers include e.g. peroxidases, laccases, oxygenases, lipoxygenase (see, e.g., WO 95/26393), and/or (non-heme) haloperoxidases.

Suitable endoglucanases include: 1) An enzyme exhibiting endo-beta-1,4-glucanase activity (E.C. 3.2.1.4), with a sequence at least 90%, or at least 94%, or at least 97% or at least 99%, or 100% identity to the amino acid sequence of positions 1-773 of SEQ ID NO:2 in WO 02/099091; or a fragment thereof that has endo-beta-1,4-glucanase activity. GAP in the GCG program determines identity using a GAP creation penalty of 3.0 and GAP extension penalty of 0.1. See WO 02/099091 by Novozymes A/S on Dec. 12, 2002, e.g., Celluclean™ by Novozymes A/S. GCG refers to sequence analysis software package (Accelrys, San Diego, Calif., USA). GCG includes a program called GAP which uses the Needleman and Wunsch algorithm to find the alignment of two complete sequences that maximizes the number of matches and minimizes the number of gaps; and 2) Alkaline endoglucanase enzymes described in EP 1 350 843A published by Kao on Oct. 8, 2003 ([0011]-[0039] and examples 1-4).

Suitable lipases include those produced by *Pseudomonas* and *Chromobacter*, and LIPOLASE®, LIPOLASE ULTRA®, LIPOPRIME® and LIPEX® from Novozymes. See also Japanese Patent Application 53-20487, laid open on Feb. 24, 1978, available from Areario Pharmaceutical Co. Ltd., Nagoya, Japan, under the trade name Lipase P "Amano". Other commercial lipases include Amano-CES, lipases ex *Chromobacter viscosum*, available from Toyo Jozo Co., Tagata, Japan; and *Chromobacter viscosum* lipases from U.S. Biochemical Corp., U.S.A. and Diosynth Co., The Netherlands, and lipases ex *Pseudomonas gladioli*. Also suitable are cutinases [EC 3.1.1.50] and esterases.

Enzymes useful for liquid detergent formulations, and their incorporation into such formulations, are disclosed in U.S. Pat. No. 4,261,868 to Hora, et al., issued Apr. 14, 1981. In an embodiment, the liquid composition herein is substantially free of (i.e. contains no measurable amount of) wild-type protease enzymes. A typical combination is an enzyme cocktail that may comprise, for example, a protease and lipase in conjunction with amylase. When present in a cleaning composition, the aforementioned additional enzymes may be present at levels from about 0.00001% to about 2%, from about 0.0001% to about 1% or even from about 0.001% to about 0.5% enzyme protein by weight of the composition.

Enzyme Stabilizers

Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

A useful enzyme stabilizer system is a calcium and/or magnesium compound, boron compounds and substituted boric acids, aromatic borate esters, peptides and peptide derivatives, polyols, low molecular weight carboxylates, relatively hydrophobic organic compounds [e.g. certain esters, diakyl glycol ethers, alcohols or alcohol alkoxylates], alkyl ether carboxylate in addition to a calcium ion source, benzamidine hypochlorite, lower aliphatic alcohols and carboxylic acids, N,N-bis(carboxymethyl) serine salts; (meth) acrylic acid-(meth)acrylic acid ester copolymer and PEG; lignin compound, polyamide oligomer, glycolic acid or its salts; poly hexa methylene bi guanide or N,N-bis-3-aminopropyl-dodecyl amine or salt; and mixtures thereof. The detergent may contain a reversible protease inhibitor e.g., peptide or protein type, or a modified subtilisin inhibitor of family VI and the plasminostrepin; leupeptin, peptide trifluoromethyl ketone, or a peptide aldehyde. Enzyme stabilizers are present from about 1 to about 30, or from about 2 to about 20, or from about 5 to about 15, or from about 8 to about 12, millimoles of stabilizer ions per liter.

Catalytic Metal Complexes

Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936; 5,595,967. Such cobalt catalysts are readily prepared by known procedures, such as taught for example in U.S. Pat. Nos. 5,597,936, and 5,595,967.

Compositions herein may also suitably include a transition metal complex of ligands such as bispidones (WO 05/042532 A1) and/or macropolycyclic rigid ligands (MRL). As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo [6.6.2] hexadecane.

Suitable transition metal MRLs are readily prepared by known procedures, such as taught for example in WO 00/32601, and U.S. Pat. No. 6,225,464.

Solvents

Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof. In some embodiments, the solvent includes water. The water can include water from any source including deionized water, tap water, softened water, and combinations thereof. Solvents are typically present at from about 0.1% to about 50%, or from about 0.5% to about 35%, or from about 1% to about 15% by weight.

In some embodiments, the composition includes less than about 10%, less than about 5% or less than about 1% any additional surfactant. The use of additional surfactant may be limited because the selected foaming compositions are capable of producing and maintaining foam without needing help from additional surfactants.

In some embodiments, the composition includes less than about 10%, less than about 5% or less than about 1% any additional silicone materials.

In some embodiments, the composition includes less than about 10%, less than about 5% or less than about 1% any foam stabilizers.

In some embodiments, the composition may be free or substantially free of additional surfactant, additional silicone material, or foam stabilizer.

Form of the Compositions

The detergent compositions may be of any suitable form, including paste, liquid, solid (such as tablets, powder/granules), foam or gel, with powders and tablets being preferred. The composition may be in the form of a unit dose product, i.e. a form which is designed to be used as a single portion of detergent composition in a washing operation. Of course, one or more of such single portions may be used in a cleaning operation.

Solid forms include, for example, in the form of a tablet, rod, ball or lozenge. The composition may be a particulate form, loose or pressed to shape or may be formed by injection moulding or by casting or by extrusion. The composition may be encased in a water-soluble wrapping, for, example of PVOH or a cellulosic material. The solid product may be provided as a portioned product as desired.

The composition may also be in paste, gel or liquid form, including unit dose (portioned products) products. Examples include a paste, gel or liquid product at least partially surrounded by, and preferably substantially enclosed in, a water-soluble coating, such as a polyvinyl alcohol package. This package may for instance take the form of a capsule, a pouch or a molded casing (such as an injection molded casing) etc. Preferably the composition is substantially surrounded by such a package, most preferably totally surrounded by such a package. Any such package may contain one or more product formats as referred to herein and the package may contain one or more compartments as desired, for example two, three or four compartments.

If the composition is a foam, a liquid or a gel it is preferably an aqueous composition although any suitable solvent may be used. According to an especially preferred embodiment of the present disclosure the composition is in the form of a tablet, most especially a tablet made from compressed particulate material.

If the compositions are in the form of a viscous liquid or gel, they preferably have a viscosity of at least 50 mPas when measured with a Brookfield RV Viscometer at 25° C. with Spindle 1 at 30 rpm.

The compositions of the disclosure will typically be used by placing them in a detergent dispenser e.g. in a dishwasher machine draw or free-standing dispensing device in an automatic dishwashing machine. However, if the composition is in the form of a foam, liquid or gel then it may be applied to by any additional suitable means into the dishwashing machine, for example by a trigger spray, squeeze bottle or an aerosol.

Processes of Making Cleaning Compositions

The compositions of the disclosure may be made by any suitable method depending upon their format. Suitable manufacturing methods for detergent compositions are well known in the art, non-limiting examples of which are described in U.S. Pat. Nos. 5,879,584; 5,691,297; 5,574,005; 5,569,645; 5,565,422; 5,516,448; 5,489,392; and 5,486,303. Various techniques for forming detergent compositions in solid forms are also well known in the art, for example, detergent tablets may be made by compacting granular/particular material and may be used herein.

In one aspect, the liquid detergent compositions disclosed herein may be prepared by combining the components thereof in any convenient order and by mixing, e.g., agitating, the resulting component combination to form a phase stable liquid detergent composition. In one aspect, a liquid matrix is formed containing at least a major proportion, or even substantially all, of the liquid components, with the liquid components being thoroughly admixed by imparting shear agitation to this liquid combination. For example, rapid stirring with a mechanical stirrer may usefully be employed. While shear agitation is maintained, substantially all of any anionic surfactant and the solid ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills are incorporated. As a variation of the composition preparation procedure described above, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

Th is more particularly described in the following examples that are intended as illustrations only, since numerous modifications and variations within the scope of the present disclosure will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques. All references cited herein are hereby incorporated in their entirety by reference.

EXAMPLES

Embodiments of the present disclosure are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Materials used in the following Examples are provided herein:

Silicone 350 cst: polydimethylsiloxane with viscosity of 350 cSt at 25° C.
Silicone 150 cst: polydimethylsiloxane with viscosity of 150 cSt at 25° C.
Silicone 0.65 cst: hexamethyldisiloxane
Silicone 1 cst: octamethyltrisiloxane
Tween 20: polysorbate 20
Tween 80: polysorbate 80
SLES: Sodium lauryl ether sulfate
Barlox 12: cocoamine oxide surfactant
Triton X-100: polyethylene glycol p-(1,1,3,3-tetramethylbutyl)-phenyl ether
Tomamine AO-728: amine oxide
Tomamine DA-17: isotridecylocypropyl-1,3-diaminopropane
Pluronic 68: EO PO block copolymer
Marlowet 4539LF: oxirane, methyl-, polymer with oxirane, carboxymethyl nonyl ether, branched
Tergitol 15-S-7: C12-C14-secondary ethoxylated alcohol
Alfoterra 123-8S: Alcohol propoxysulfate
Cola Lipid DCCA: Sodium Coco PG-Dimonium Chloride Phosphate Example 1

Alkyl modified siloxane and siloxanes alone are not known to be able to form a foam in solutions of an organic solvent, such as ethanol, and a polar solvent, such as water. Without being bound to a particular theory, but as shown in FIG. 1, it is thought that siloxanes do not have surface activity for ethanol, water, or an ethanol/water solution and cannot reduce the surface tension of these solutions. Due to this lack of surface activity, and lack of a reduction in surface tension, siloxanes on their own should not be capable of acting as a foam agent.

In order to screen for possible foaming in an ethanol/water solution, manual foam testing was conducted on alkyl modified siloxane or siloxane alone. To test, 20 mL of each of the compositions found in Table 1 were placed in a 1 inch by 4.5 inch glass cylinder bottle and then shaken for about 10 seconds. After shaking, all the compositions lost all foaming within about 10 seconds. This indicates that a wide variety of alkyl modified polysioxane alone are unable to produce stable foam.

This lack of foaming is likely due to the lack of surface activity. Without being bound to a particular theory, the lack of surface activity may be due to the low surface tension of the ethanol. Few surfactants, such as silicone- and fluoride-based, are capable of reducing the surface tension of water to equal that of the surface tension of ethanol, making it energetically beneficial to form new surface area through the foaming action. However, without surface activity, siloxanes cannot act as silicone surfactants to form a foam, and thus behave differently than silicone surfactants, even if both are silicone based and siloxanes have a lower surface tension than ethanol.

This lack of surfactant ability of siloxanes may be due to their insolubility in water and/or ethanol. While some, such as C8 methicone, are soluble in ethanol, an ethanol/water solution reduces their solubility such that the siloxane may not dissolve and therefore may not have any surface activity. Therefore, siloxanes, unlike other silicone-based compounds, may not act as a surfactant nor produce a stable foam in a water/ethanol solution when used alone.

TABLE 1

|  | Example 1 | Example 2 | Example 3 | Example 4 | Example 5 | Example 6 | Example 7 |
|---|---|---|---|---|---|---|---|
| Caprylyl Methicone | 2% | | | | | | |
| Silicone cst 150 | | 2% | | | | | |
| Silicone cst 350 | | | 2% | | | | |
| C26-28 Alkyl Dimethicone, melting point 35° C. | | | | Solid does no dissolve | | | |
| Cyclotetrasiloxane | | | | | 2% | | |
| Cetyl Dimethicone | | | | | | 2% | |
| Stearyl Dimethicone | | | | | | | Solid does no dissolve |
| C26-28 Alkyl Methicone, melting point 70° C. | | | | | | | |
| Alkylaryl polysiloxane fluid (insoluble in ethanol) | | | | | | | |
| Alkylaryl polysiloxane fluid (soluble in ethanol) | | | | | | | |
| Silicone cst 0.65 | | | | | | | |
| Silicone cst 1 | | | | | | | |
| Ethyl Methicone | | | | | | | |
| Ethanol SDA-40B 190 proof (92.3% active) | 62% | 62% | 62% | 62% | 62% | 62% | 62% |
| Di-Water | 37.8% | 36% | 36% | 38% | 36% | 36% | 38% |
| Observation | Cloudy solution, Foam disappeared in 10 seconds. | Cloudy solution, Foam disappeared in 10 seconds. | Cloudy solution, Foam disappeared in 10 seconds. | Foam disappeared in 10 seconds. | Cloudy solution, Foam disappeared in 10 seconds. | Cloudy solution, Foam disappeared in 10 seconds. | Foam disappeared in 10 seconds. |

|  | Example 8 | Example 9 | Example 10 | Example 11 | Example 12 | Example 13 |
|---|---|---|---|---|---|---|
| Caprylyl Methicone | | | | | | |
| Silicone cst 150 | | | | | | |
| Silicone cst 350 | | | | | | |
| C26-28 Alkyl Dimethicone, melting point 35° C. | | | | | | |
| Cyclotetrasiloxane | | | | | | |
| Cetyl Dimethicone | | | | | | |
| Stearyl Dimethicone | | | | | | |
| C26-28 Alkyl Methicone, melting point 70° C. | Solid does no dissolve | | | | | |
| Alkylaryl polysiloxane fluid (insoluble in ethanol) | | 2% | | | | |
| Alkylaryl polysiloxane fluid (soluble in ethanol) | | | 2% | | | |
| Silicone cst 0.65 | | | | 2% | | |
| Silicone cst 1 | | | | | 2% | |
| Ethyl Methicone | | | | | | 2% |

TABLE 1-continued

| | | | | | | |
|---|---|---|---|---|---|---|
| Ethanol SDA-40B 190 proof (92.3% active) | 62% | 62% | 62% | 62% | 62% | 62% |
| Di-Water | 38% | 36% | 36% | 36% | 36% | 36% |
| Observation | Foam disappeared in 10 seconds. | Cloudy solution, Foam disappeared in 10 seconds. | Cloudy solution, Foam disappeared in 10 seconds. | Cloudy solution, Foam disappeared in 10 seconds | Cloudy solution, Foam disappeared in 10 seconds | Cloudy solution, Foam disappeared in 10 seconds |

Example 2

Figure 2:
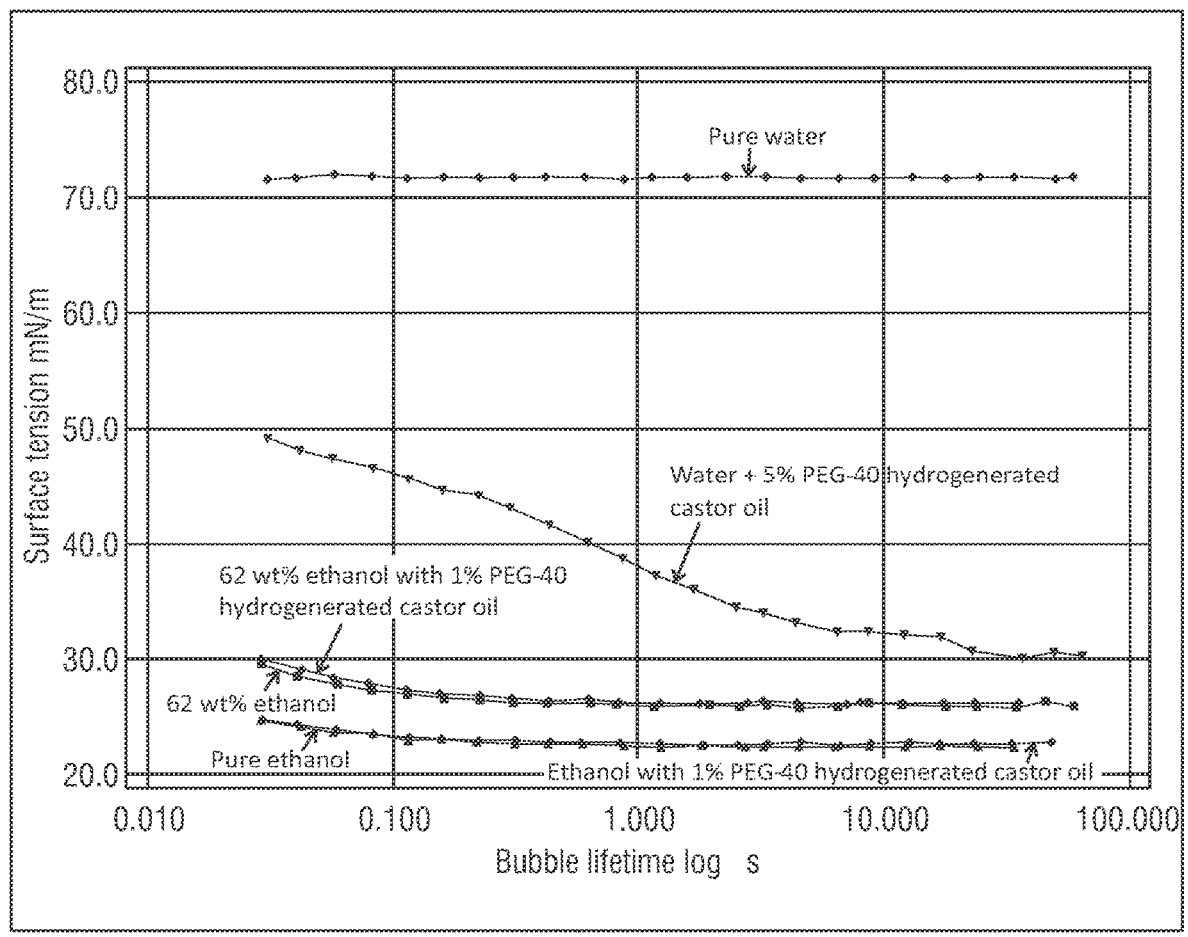
FIG. 2 shows a graphical representation of the results of dynamic surface tension analysis indicate that PEG-40 hydrogenated castor oil reduces the surface tension of pure water to 30 mN/m$^2$ at 5 wt-% concentration. However, it has no impact on surface tension for ethanol and 62 wt-% Ethanol SDA-40B 190 proof (92.3% active) solution.

Modified castor oil is not known to be able to produce a stable foam in solutions of organic solvents, such as pure ethanol, or solutions of organic solvents mixed with polar solvents, such as ethanol/water solutions. Without being bound to a particular theory, as shown in FIG. 2, PEG modified castor oil, while able to reduce the surface tension of pure water, may not be surface active in an alcohol, such as pure ethanol or a water/ethanol solution. Further, not all castor oils are soluble in alcohols. Due to the lack of surface activity in organic solvents or solutions containing organic solvents and/or the being insoluble, modified castor oils alone should not be able to form stable foam in ethanol/water solutions.

In order to screen for possible forming of modified castor oil in an ethanol/water solution when used alone, manual foam testing was conducted on various modified castor oils. To screen the various modified castor oils, 20 mL of each of the compositions found in Table 2 were placed in a 1 inch by 4.5 inch glass cylinder bottle and then shaken for about 10 seconds. After shaking, all the compositions lost all foaming within about 20 seconds. This indicates PEG modified castor oil alone was unable to produce stable foam in the ethanol/water solutions.

The lack of foaming seen by the PEG modified castor oil is likely due to the lack of surface activity in ethanol, making it energetically unfavorable to increase the surface area of the solution. However, even if the castor oil is surface active, it still fails to reduce the surface tension of either a pure ethanol solution or a 62% ethanol/water solution Additionally, this lack of foaming may also be due to a lack of solubility for some modifications. For example, 10 moles EO modifications was insoluble in the 62% ethanol/water solution. However, when increasing to a 20 to 60 moles EO modification, the modified castor oil is soluble enough to enter the solution. As indicated by Table 2, even when sufficiently soluble to enter solution, the PEG modified castor oils still were unable to form a stable foam when used alone.

Therefore, neither a pendent alkyl siloxane nor a PEG-modified castor oil alone may cause stable foaming in ethanol/water solutions and may not be able to replace the known surfactants for these solutions.

TABLE 2

| | Example 11 | Example 12 | Example 13 | Example 14 | Example 15 | Example 16 |
|---|---|---|---|---|---|---|
| PEG-10 Hydrogenated Castor Oil | 3% | | | | | |
| PEG-20 Hydrogenated Castor Oil | | 3% | | | | |
| PEG-40 Hydrogenated Castor Oil | | | 3% | | | |
| PEG-50 Hydrogenated Castor Oil | | | | 3% | | |
| PEG-60 Hydrogenated Castor Oil | | | | | 3% | |
| PEG-40 Castor Oil | | | | | | 3% |
| Ethanol SDA-40B 190 proof (92.3% active) | 62% | 62% | 62% | 62% | 62% | 62% |
| Di-Water | 35% | 35% | 35% | 37.8% | 36% | 36% |
| Observation | Cloudy solution, Foam disappeared in 20 seconds. | Clear solution, Foam disappeared in 20 seconds. | Clear solution, Foam disappeared in 20 seconds. | Clear solution, Foam disappeared in 20 seconds. | Clear solution, Foam disappeared in 20 seconds. | Clear solution, Foam disappeared in 20 seconds. |

Example 3

As neither the alkyl modified siloxane nor the PEG modified castor oil alone was able to reduce the surface tension sufficiently in the water/alcohol solutions above, one would not expect together they would act in synergy to reduce the surface tension sufficiently for foam to form.

Manual foam testing was conducted to screen for foaming of PEG modified castor oil with alkyl modified siloxane or siloxane/polydimethylsiloxane. Twenty mL of each of the compositions found in Table 3 were placed in a 1 inch by 4.5 inch glass cylinder bottle and then shaken for about 10 seconds.

Figure 3:
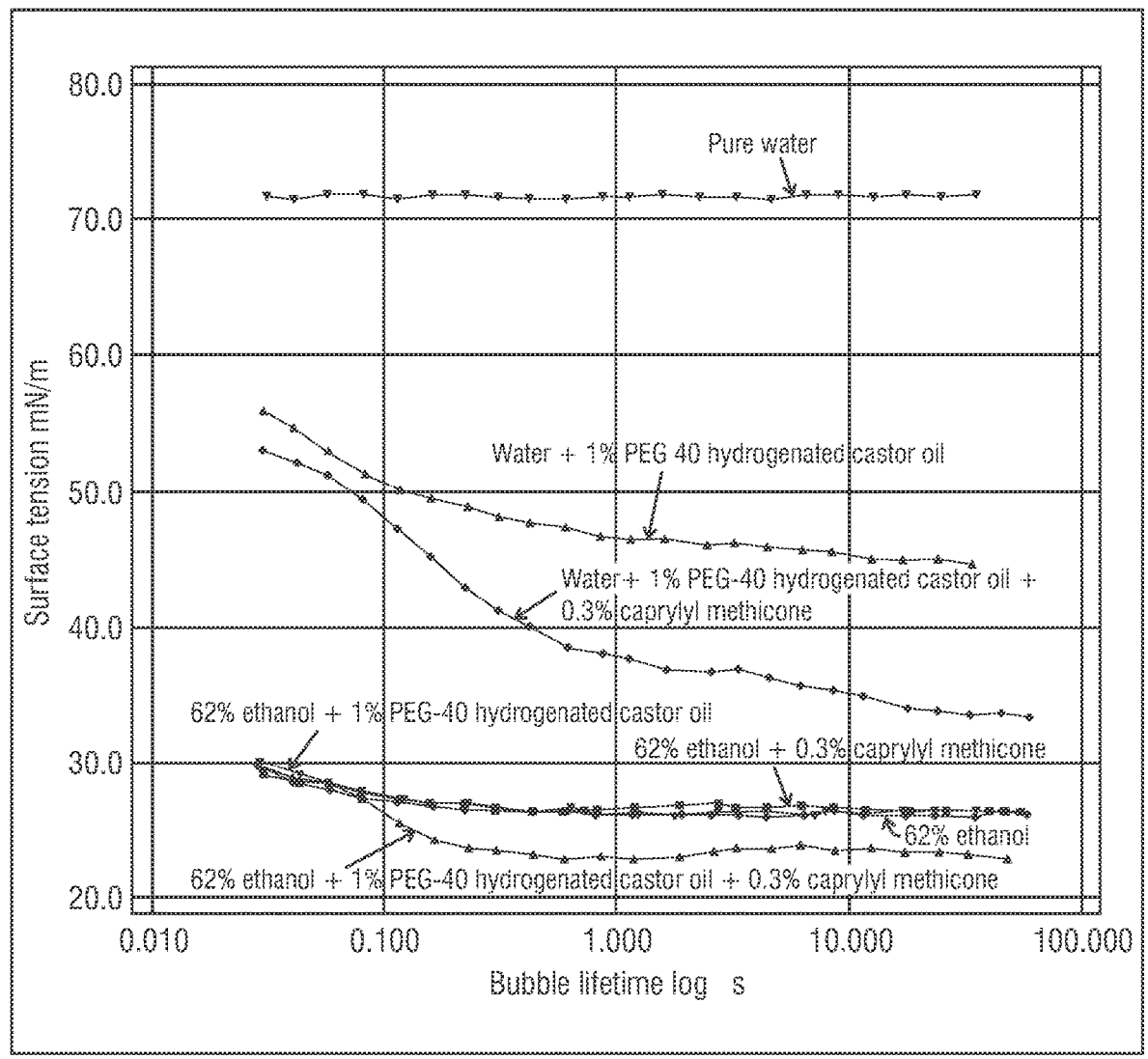
FIG. 3 shows a graphical representation of the results of dynamic surface tension analysis indicate that PEG-40 hydrogenated castor oil combined with caprylyl methicone could further reduce the surface tension of water and 62 wt % Ethanol SDA-40B 190 proof (92.3% active) solution.

After shaking, the compositions with a combination of PEG-modified castor oil and caprylyl methicone were able to produce a stable foam. When a small amount of C26-C28 alkyl dimethicone dissolved with PEG-modified castor oil in a 62% ethanol solution, it produced stable foam. Further the cyclotetrasiloxance (D4) combined with EG-modified castor oil produces a stable foam. However, this combination required a higher concentration compared with the caprylyl methicone. Additionally, the fresh solutions of silicone oil (150 cst and 350 cst) with PEG-modified castor oil produced low foams lasting 10 minutes. The silicone droplets phase separated from the solution and no foam was from an overnight solution. These results show that, surprisingly, PEG-40 hydrogenated castor oil may work with a wide range of hydrophobic siloxanes over a range of concentrations as a foaming composition when using both alone failed. Additionally, as shown in FIG. 3, the foaming composition was able to lower the surface tension of water, showing that PEG-40 hydrogenated castor oil coupled with caprylyl methicone may function as a surfactant in water-based solutions.

Therefore, unlike when PEG modified castor oil or alkyl modified siloxance or siloxane/polymethylsiloxane alone could not produce foam, the combination produced a stable foam. Without being bound to a particular theory, the pendent alkyl chains of the siloxanes may interact with the hydrophobic regions of the castor oil tails. Further, the PEG-modified region of the castor oil increases the solubility of the composition in the aqueous portion of the solution. It may also allow for more adsorption at the liquid-liquid interface of the water/alcohol solution. This interaction may increase the surface activity of the composition in the water/alcohol solution, allowing it to lower the surface tension of the solutions sufficiently enough to make it energetically favorable to create foam and to allow the composition to act as a surfactant.

Further, the hydrophobicity of both the castor oil and siloxanes may allow the foaming composition to act as a surfactant in other water/organic solvent based solutions, or in other hydrophobic solutions, such as hydrocarbon condensates. Additionally, the ability of PEG-40 hydrogenated castor oil to increase the solubility of the hydrophobic siloxane may allow it to solubilize other hydrophobic compounds, like unmodified triglycerides and transfats in a water based system.

TABLE 3

|  | Example 1 | Example 2 | Example 3 | Example 4 | Example 5 | Example 6 | Example 7 |
|---|---|---|---|---|---|---|---|
| PEG-40 Hydrogenated Castor Oil | 3% | 3% | 3% | 3% | 3% | 3% | 3% |
| Caprylyl Methicone (C8 trisiloxane) | 0.2% | | | | | | |
| C26-28 Alkyl Dimethicone, melting point 35° C. | | 3% (most remain as undissolved solid) | | | | | |
| Cyclotetrasiloxane | | | 3% | | | | |
| Cetyl Dimethicone | | | | 1% | | | |
| Stearyl Dimethicone | | | | | 3% (most remain as undissolved solid) | | |
| C26-28 Alkyl Methicone, melting point 70° C. | | | | | | 3% (most remain as undissolved solid) | |
| Alkylaryl polysiloxane fluid (insoluble in ethanol) | | | | | | | 1% |
| Alkylaryl polysiloxane fluid (soluble in ethanol) | | | | | | | |
| Silicone 350 cst | | | | | | | |
| Silicone 150 cst | | | | | | | |
| Silicone 0.65 cst | | | | | | | |
| Silicone 1 cst | | | | | | | |
| Ethyl Methicone | | | | | | | |

TABLE 3-continued

| | | | | | | | |
|---|---|---|---|---|---|---|---|
| Ethanol SDA-40B 190 proof (92.3% active) | 62% | 62% | 62% | 62% | 62% | 62% | 62% |
| Di-Water | 34.8% | 32% | 32% | 32% | 32% | 32% | 34% |
| Observation | Clear solution, Initial foam height was about 15 mm, lasted more than 30 minutes. | Small amount of C26-28 alkyl dimethicone was dissolved in solution, Initial foam height 10 mm, lasted more than 10 minutes. | Initial foam height was about 15 mm, lasted more than 30 minutes. | Cloudy solution, Foam disappeared in 20 seconds. | Steryl Diethicone did not dissolve in soultion, Clear solution, Foam disappeared in 20 seconds. | C26-28 Alkyl Methicone did not dissolve in soultion, Clear solution, Foam disappeared in 20 seconds. | Cloudy solution, Foam disappeared in 20 seconds. |

| | Example 8 | Example 9 | Example 10 | Example 11 | Example 12 | Example 13 |
|---|---|---|---|---|---|---|
| PEG-40 Hydrogenated Castor Oil | 3% | 3% | 6% | 1% | 1% | 1% |
| Caprylyl Methicone (C8 trisiloxane) | | | | | | |
| C26-28 Alkyl Dimethicone, melting point 35° C. | | | | | | |
| Cyclotetrasiloxane | | | | | | |
| Cetyl Dimethicone | | | | | | |
| Stearyl Dimethicone | | | | | | |
| C26-28 Alkyl Methicone, melting point 70° C. | | | | | | |
| Alkylaryl polysiloxane fluid (insoluble in ethanol) | | | | | | |
| Alkylaryl polysiloxane fluid (soluble in ethanol) | 1% | | | | | |
| Silicone 350 cst | | 1% | | | | |
| Silicone 150 cst | | | 1% | | | |
| Silicone 0.65 cst | | | | 0.5% | | |
| Silicone 1 cst | | | | | 0.5% | |
| Ethyl Methicone | | | | | | 0.5% |
| Ethanol SDA-40B 190 proof (92.3% active) | 62% | 62% | 62% | 62% | 62% | 62% |
| Di-Water | 34% | 34% | 34% | 36.5% | 36.5% | 36.5% |
| Observation | Cloudy solution, Foam disappeared in 20 seconds. | Cloudy solution, Fresh solution could produce foam lasting for 10 minutes. For overnight solution, the foam disappeared in 20 seconds. | Cloudy solution, Fresh solution could produce foam lasting for 10 minutes. For overnight solution, the foam disappeared in 20 seconds. | Clear solution, Initial foam height was about 15 mm, lasted more than 30 minutes, | Cloudy solution, Initial foam height was about 15 mm, lasted more than 30 minutes, | Clear solution, Initial foam height was about 15 mm, lasted more than 30 minutes, |

Example 4

As PEG-40 hydrogenated castor oil was sufficient to allow various siloxanes to foam alcohol/water solutions, various other PEG substitutions were tested with caprylyl methicone using manual foam testing. Twenty mL of each of the compositions found in Table 4 were placed in a 1 inch by 4.5 inch glass cylinder bottle and then shaken for about 10 seconds.

After shaking, the compositions with the combination of PEG modified castor oil and caprylyl methicone could produce stable foams in 62 wt % ethanol solutions. The PEG modified castor oils with 20, 50, and 60 EO moles produced stable foams with a close initial height to that of the 40 EO moles castor oil. The 20 moles oil produced lower, but still stable, foam, and the 10 moles oil produced unstable foam. Therefore, a longer hydrophilic region did not interfere with the hydrophobic interactions between the castor oil and the siloxane. However, as indicated by the 10 EO mole modification, an insufficiently long hydrophilic region may not allow sufficient solubilization of the siloxane. Also, higher concentrations of PEG-modified castor oil with alkyl modified polysiloxane did not boost initial foam height, so additional hydrotropes or surfactants should not interfere with foam height.

The lower, but stable height of the 20 moles modification when compared to the longer modifications of the cast oil also shows that foam height may be controlled. This is important for some systems that require low foaming or in rinse aids.

Comparing the PEG-40 hydrogenated castor oil to the PEG-40 castor oil, the PEG-40 castor oil produced less stable foam with a lower initial height. Without being bound to a particular theory, this is likely due to the backbone of PEG-40 being stiffer due to unsaturated double-bonding. This may prevent the tails of the PEG-40 castor oil to interact sufficiently with the pendent alkyl groups of the caprylyl methicone to allow the caprylyl methicone to solubilize sufficiently with the water present in the solution.

Additionally, the addition of salts does not appear to have an effect on foam height. The addition of either potassium chloride or a 5 grain water did not show an effect on the height of the foam nor the stability of the foam. Therefore, the foaming compositions may be tolerant in hard waters and with additional agents.

Therefore, depending on the PEG-modified castor oil when used with a siloxane, such as caprylyl methicone, the foam height and stability may be tailored to a desirable level. This may allow one to more tailor the composition toward a detergent where high foaming is desired, or a rinse aid, when low foaming may be desired.

TABLE 4

| | Example 1 | Example 2 | Example 3 | Example 4 | Example 5 | Example 6 | Example 7 | Example 8 | Example 9 |
|---|---|---|---|---|---|---|---|---|---|
| PEG-10 Hydrogenated Castor Oil | 1% | | | | | | | | |
| PEG-20 Hydrogenated Castor Oil | | 1% | | | | | | | |
| PEG-40 Hydrogenated Castor Oil | | | 1% | | | | 5% | 1% | 1% |
| PEG-50 Hydrogenated Castor Oil | | | | 1% | | | | | |
| PEG-60 Hydrogenated Castor Oil | | | | | 1% | | | | |
| PEG-40 Castor Oil | | | | | | 1% | | | |
| Caprylyl Methicone | 0.1% | 0.1% | 0.1% | 0.1% | 0.1% | 0.1% | 1% | 0.1% | 0.1% |
| Ethanol SDA-40B 190 proof (92.3% active) | 62% | 62% | 62% | 62% | 62% | 62% | 62% | 62% | 62% |
| Di-Water | 36.9% | 36.9% | 36.9% | 36.9% | 36.9% | 36.9% | 32% | | |
| 10 mM KCL solution | | | | | | | | 36.9% | |
| 5 grain water | | | | | | | | | 36.9% |
| Observation | Cloudy solution, Foam disappeared in 20 seconds. | Clear solution, Initial foam was about 10 mm, lasted more than 30 minutes. | Clear solution, Initial foam height was about 15 mm, lasted more than 30 minutes. | Clear solution, Initial foam height about 15 mm, lasted more than 30 minutes. | Clear solution, Initial foam height about 15 mm, lasted more than 30 minutes. | Clear solution, Initial foam height about 13 mm, lasted more than 10 minutes. | Cloudy solution, Initial foam height about 15 mm, lasted more than 30 minutes. | Clear solution, Initial foam height about 15 mm, lasted more than 30 minutes. | Clear solution, Initial foam height about 15 mm, lasted more than 30 minutes. |

Example 5

To further characterize the foaming characteristics of the synergistic compositions, the concentrations of the PEG modified castor oil and caprylyl methicone were altered across their lower ranges. Additionally, the amount of ethanol in some of the compositions was increased to test foaming in higher concentrations of ethanol. Twenty mL of each of the compositions found in Tables 5-7 were placed in a 1 inch by 4.5 inch glass cylinder bottle and then shaken for about 10 seconds.

After shaking, as shown in Table 5, it was possible to produce foam in up to a 74 wt % ethanol solution with sufficient PEG modified castor oil and caprylyl methicone. A 1.3% PEG-40 hydrogenated castor oil and 0.4% caprylyl methicone combination was able to stably form foam for more than 12 minutes in an 80 wt % ethanol solution (See Table 5). As ethanol has a very low surface tension, this shows the foaming compositions will work over a range of solutions as it was shown above that the compositions would also foam water, which has a high surface tension given its polar nature. However, while PEG-40 hydrogenated castor oil may be too hydrophilic to fully act as a foam producer with caprylyl methicone in nearly pure ethanol, the composition may still work as a surfactant replacement composition in mixed solutions.

At 62 wt % ethanol, the lowest concentration of PEG-modified castor oil able to produce a stable foam was between 0.2% to 0.3% in combination with 0.7% caprylyl methicone (see Table 6). For caprylyl methicone, the lowest concentration to produce stable foam in a 62 wt % ethanol solution was between 0.05% to 0.07% in combination with 3% PEG-40 hydrogenated castor oil (see Table 7). Thus, a low amount of both compounds is sufficient to cause foaming in low surface tension solutions.

TABLE 5

|  | Example 1 | Example 2 | Example 3 | Example 4 | Example 5 | Example 6 | Example 7 |
|---|---|---|---|---|---|---|---|
| PEG-40 Hydrogenated Castor Oil | 1.5% | 1.5% | 1.5% | 1.4% | 1.3% | 1.3% | 1.3% |
| Caprylyl Methicone | 0.5% | 0.5% | 0.5% | 0.4% | 0.4% | 0.4% | 0.4% |
| Ethanol SDA-40B 190 proof (92.3% active) | 98% | 95% | 92% | 89% | 86% | 83% | 80% |
| Di-Water |  | 3% | 6% | 9.2% | 12.3% | 36.3% | 18.3% |
| Observation | Foam disappeared in 5 seconds. | Foam disappeared in 5 seconds. | Foam disappeared in 10 seconds. | Foam disappeared in 10 seconds. | Foam disappeared in 10 seconds. | Foam disappeared in 20 seconds. Some small bubbles attached to glass wall lasted 1 minute, | Stable Foam more than 12 minutes. |

TABLE 6

|  | Example 8 | Example 9 | Example 10 | Example 11 | Example 12 | Example 13 | Example 14 |
|---|---|---|---|---|---|---|---|
| PEG-40 Hydrogenated Castor Oil | 1.6% | 0.8% | 0.6% | 0.3% | 0.15% | 0.08% | 0.04% |
| Caprylyl Methicone | 0.7% | 0.7% | 0.7% | 0.7% | 0.7% | 0.7% | 0.7% |
| Ethanol SDA-40B 190 proof (92.3% active) | 62% | 62% | 62% | 62% | 62% | 62% | 62% |
| Di-Water | 35.7% | 36.7% | 37.1% | 37.3% | 37.55% | 37.2% | 37.3% |
| Observation | Stable Foam. | Stable Foam. | Stable Foam. | Stable Foam. | Less foam, stable. | Much less foam. | Foam disappeared in 10 seconds. |

TABLE 7

|  | Example 15 | Example 16 | Example 17 | Example 18 | Example 20 |
|---|---|---|---|---|---|
| PEG-40 Hydrogenated Castor Oil | 3% | 3% | 3% | 3% | 3% |
| Caprylyl Methicone | 0.2% | 0.1% | 0.07% | 0.05% | 0.03% |
| Ethanol SDA-40B 190 proof (92.3% active) | 62% | 62% | 62% | 62% | 62% |
| Di-Water | 34.8% | 34.9% | 34.93% | 34.95% | 34.97% |

TABLE 7-continued

|  | Example 15 | Example 16 | Example 17 | Example 18 | Example 20 |
|---|---|---|---|---|---|
| Observation | Stable Foam. | Stable Foam. | Stable Foam. | Less Stable Foam. | Foam disappeared in 10 seconds. |

Example 6

As excess PEG-modified castor oil did not appear to have an effect on foaming, other hydrotropes and surfactants should be able to be added to the composition without interfering with foaming. In order to test the foaming with additional compounds in the compositions, additional surfactants were added to composition comprising 0.2% caprylyl methicone, 3% to 4% PEG-40 hydrogenated castor oil, and 62 wt % ethanol. Twenty mL of each of the compositions found in Tables 8 and 9 were placed in a 1 inch by 4.5 inch glass cylinder bottle and then shaken for about 10 seconds.

Depending on the surfactant, the addition of additional surfactants either had no effect on initial foam height or, in high enough concentrations, the additional surfactants decreased the initial foam height and stability. For example, Bartox 12 at 2% had no effect on initial height or stability, but at 6% the foam disappeared within 20 seconds (see Table 8). Similarly, when the concentration of Tomamine AO-728 was increased from 1% to 5%, the higher concentration resulted in the loss of foaming within 20 seconds (see Table 9). However, for some surfactants, such as extended $C_{10}PO_8EO_6$ an increase in the concentration did not affect foam height or stability (see Table 8).

Therefore, additional surfactants, even in high amounts, may be added to the compositions without losing the loss of foam stability in order to increase the detergency. Further, surfactants may be added to control foam height for certain applications, such as use in a rinse aid.

TABLE 8

|  | Example 1 | Example 2 | Example 3 | Example 4 | Example 5 | Example 6 | Example 7 | Example 8 | Example 9 | Example 10 |
|---|---|---|---|---|---|---|---|---|---|---|
| Caprylyl Methicone | 0.2% | 0.2% | 0.2% | 0.2% | 0.2% | 0.2% | 0.2% | 0.2% | 0.2% | 0.2% |
| PEG-40 Hydrogenated Castor Oil | 3% | 3% | 3% | 3% | 3% | 3% | 3% | 3% | 3% | 3% |
| Tween 20 | 3% |  | 1.5% |  |  |  |  |  |  |  |
| Tween 80 |  | 3% | 1.5% |  |  |  |  |  |  |  |
| PEG-400 |  |  |  | 3% |  |  |  |  |  |  |
| Extended $C_{10}PO_8EO_6$ |  |  |  |  | 2% | 6% |  |  |  |  |
| SLES (60%) |  |  |  |  |  |  | 2% | 6% |  |  |
| Barlox 12 (30%) |  |  |  |  |  |  |  |  | 2% | 6% |
| Ethanol SDA-40B 190 proof (92.3% active) | 62% | 62% | 62% | 62% | 62% | 62% | 62% | 62% | 62% | 62% |
| Di-Water | 31.8% | 31.8% | 31.8% | 31.8% | 32.8% | 31.8% | 32.8% | 28.8% | 32.8% | 28.8% |
| Observation | Clear solution, Initial foam height was about 15 mm, lasted more than 30 minutes. | Clear solution, Initial foam height was about 15 mm, lasted more than 30 minutes. | Clear solution, Initial foam height was about 15 mm, lasted more than 30 minutes. | Clear solution, Initial foam height was about 15 mm, lasted more than 30 minutes. | Clear solution, Initial foam height was about 15 mm, lasted more than 30 minutes. | Clear solution, Initial foam height was about 15 mm, lasted more than 30 minutes. | Clear solution, Initial foam height was about 15 mm, lasted more than 30 minutes. | Clear solution, Initial foam height was about 8 mm, lasted more than 30 minutes. | Clear solution, Initial foam height was about 15 mm, lasted more than 30 minutes. | Clear solution, Foam disappeared in 20 seconds. |

TABLE 9

|  | Example 11 | Example 12 | Example 13 | Example 14 | Example 15 | Example 16 | Example 17 | Example 18 | Example 19 | Example 20 |
|---|---|---|---|---|---|---|---|---|---|---|
| Caprylyl Methicone | 0.2% | 0.2% | 0.2% | 0.2% | 0.2% | 0.2% | 0.2% | 0.2% | 1% | 1% |
| PEG-40 Hydrogenated Castor Oil | 3% | 3% | 3% | 3% | 3% | 3% | 3% | 3% | 4% | 4% |
| Triton X-100 | 1% | 5% |  |  |  |  |  |  |  |  |
| Tomamine AO-728 |  |  | 1% | 5% |  |  |  |  |  |  |
| Lecithin |  |  |  |  | 0.4% |  |  |  |  |  |
| 1% citric acid |  |  |  |  |  | 0.4% |  |  |  |  |
| 1% APG solution |  |  |  |  |  |  | 0.4% |  |  |  |
| Tomamine DA-17 |  |  |  |  |  |  |  | 1% |  |  |

TABLE 9-continued

| | Example 11 | Example 12 | Example 13 | Example 14 | Example 15 | Example 16 | Example 17 | Example 18 | Example 19 | Example 20 |
|---|---|---|---|---|---|---|---|---|---|---|
| Dicyclohexylamine | | | | | | | | | 2% | |
| Pluronic 68 | | | | | | | | | | 3% |
| Ethanol SDA-40B 190 proof (92.3% active) | 62% | 62% | 62% | 62% | 62% | 62% | 62% | 62% | 62% | 62% |
| Di-Water | 33.8% | 29.8% | 33.8% | 29.8% | 34.4% | 34.4% | 34.4% | 33.8% | 33% | 30% |
| Observation | Clear solution, Initial foam height was about 15 mm, lasted more than 30 minutes. | Clear solution, Initial foam height was about 8 mm, lasted more than 30 minutes. | Clear solution, Initial foam height was about 15 mm, lasted more than 30 minutes. | Clear solution, Foam disappeared in 20 seconds. | Lecithin does not dissolve. Cloudy solution. Foam disappeared in 20 seconds. | Clear solution, Initial foam height was about 15 mm, lasted more than 30 minutes. | Clear solution, Initial foam height was about 15 mm, lasted more than 30 minutes. | Clear solution, Initial foam height was about 15 mm, lasted more than 30 minutes. | Cloudy solution. Foam disappeared in 3 minutes. | Cloudy solution. Foam disappeared in 5 minutes. |

Example 7

As additionally surfactants did not appear to affect the foaming of the compositions in an ethanol/water solution, they may be able to be used in place of the PEG-modified castor oil to create other foaming compositions. To determine if surfactants other than PEG modified castor oil would produce foams in ethanol solutions, various other surfactants were added to a 0.2% caprylyl methicone composition in a 62 wt % ethanol solution. Twenty mL of each of the compositions found in Tables 10 and 11 were placed in a 1 inch by 4.5 inch glass cylinder bottle and then shaken for about 10 seconds. The results indicate that none of the other surfactants were capable of producing foams in the 62 wt % ethanol solution with caprylyl methicone and cannot be substituted for the modified castor oil.

In Table 12, the mixer was pumped 10 times into a 80 ml beaker through a inline pumper. In PEG-castor foaming formula. C8 trisiloxanes made a stable foam. Optimally with low molecular silicone fluid, the foam is smaller and smoother. PolyOX made the foam denser, however, it increased the pump resistance due to the increase of viscosity. PEI would make the foam stabler without increasing the mixer viscosity. VX 10035 form a microemulsion with better foam stability compared with HP20.

Figure 4:
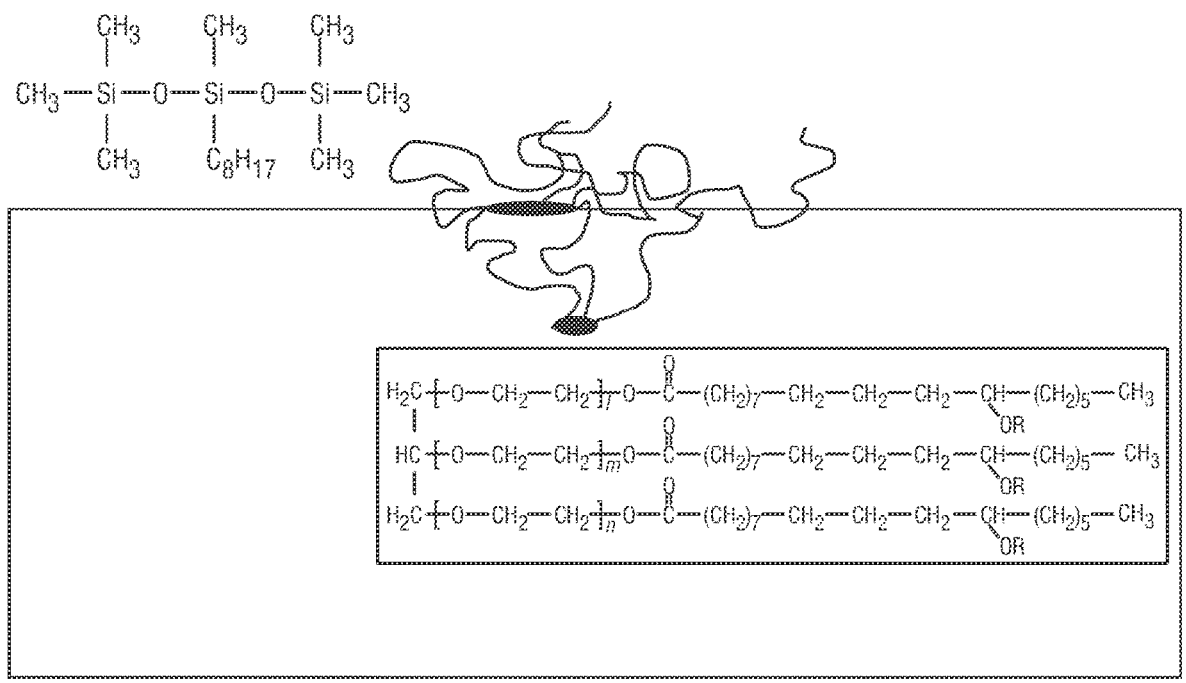
FIG. 4 shows a schematic representation of the hydrophobic interactions between the alkyl chains between the PEG-modified oil and caprylyl methicone, the small caprylyl methicone is entrapped within the cage structure of the PEG-modified oil.

This may be due to the PEG modified castor oil structure. Without being bound to a specific theory, the PEG modified castor oil structure may be able to form a cage around the siloxane, as depicted in FIG. 4. The hydrophobic ends of the three arms may provide sufficient interactions with the pendent groups of the alkyl siloxane in order to increase its solubility in the ethanol/water solution. The other surfactants may not be able to sufficiently interact with the pendent alkyl groups of the siloxane in order to provide sufficient solubility as many have only a single hydrophobic region. This also indicates that other modified triglyercide hydrotropes or surfactants may provide sufficient interactions to create foaming compositions with pendent alkyl siloxanes.

Figure 5:
FIG. 5 shows mixtures under fluorescent light. On the Left is the mixture of Example 1 with 46 ppm dye without PEG-40, on the right is Example 1 with 46 ppm dye with PEG-40. As can be seen the right bottle showed a strong and homogenous fluorescent light indicating that silicone materials (C8 trisiloxane and silicone fluid) have been completely dissolved into ethanol/water solution to form a microemulsion.

Finally FIG. 5 shows the mixtures under fluorescent light. On the Left is Example 1 with 46 ppm dye without PEG-40, on the right Right Example 1 with 46 ppm dye. As can be seen the right bottle showed a strong and homogenous fluorescent light indicating that silicone materials (C8 trisiloxane and silicone fluid) have been completely dissolved into ethanol/water solution to form a microemulsion.

TABLE 10

| | Example 1 | Example 2 | Example 3 | Example 4 | Example 5 |
|---|---|---|---|---|---|
| Caprylyl Methicone | 0.2% | 0.2% | 0.2% | 0.2% | 0.2% |
| Castor Oil | 3% | | | | |
| Extended Surfactant $C_{10}PO_8EO_6$ | | 3% | | | |
| Surfadone LP-100 | | | 3% | | |
| Tomamine DA-17 | | | | 3% | |
| Marlowet 4539LF | | | | | 3% |
| Tergitol 15-5-7 | | | | | |
| Barlox-12 30% | | | | | |
| SLES 60% | | | | | |
| Alforerra 123-85 | | | | | |
| Cola Lipid DCCA | | | | | |
| Ethanol SDA-40B 190 proof (92.3% active) | 62% | 62% | 62% | 62% | 62% |
| Di-Water | 34.8% | 34.8% | 34.8% | 34.8% | 34.8% |
| Observation | Cloudy solution, Foam | Cloudy solution, Foam | Cloudy solution, Foam | Cloudy solution, Foam | Cloudy solution, Foam |

TABLE 10-continued

|  | Example 6 | Example 7 | Example 8 | Example 9 | Example 10 |
| --- | --- | --- | --- | --- | --- |
| | disappeared in 20 seconds. | disappeared in 20 seconds. | disappeared in 20 seconds. | disappeared in 20 seconds. | disappeared in 20 seconds. |
| Caprylyl Methicone | 0.2% | 0.2% | 0.2% | 0.2% | 0.2% |
| Castor Oil Extended Surfactant $C_{10}PO_8EO_6$ | | | | | |
| Surfadone LP-100 | | | | | |
| Tomamine DA-17 | | | | | |
| Marlowet 4539LF | | | | | |
| Tergitol 15-5-7 | 3% | | | | |
| Barlox-12 30% | | 10% | | | |
| SLES 60% | | | 10% | | |
| Alforerra 123-85 | | | | 3% | |
| Cola Lipid DCCA | | | | | 3% |
| Ethanol SDA-40B 190 proof (92.3% active) | 62% | 62% | 62% | 62% | 62% |
| Di-Water | 34.8% | 27.8% | 27.8% | 34.8% | 34.8% |
| Observation | Cloudy solution, Foam disappeared in 20 seconds. | Cloudy solution, Foam disappeared in 20 seconds. | Cloudy solution, Foam disappeared in 20 seconds. | Cloudy solution, Foam disappeared in 20 seconds. | Cloudy solution, Foam disappeared in 20 seconds. |

TABLE 11

|  | Example 11 | Example 12 | Example 13 | Example 14 | Example 15 | Example 16 |
| --- | --- | --- | --- | --- | --- | --- |
| Caprylyl Methicone | 0.2% | 0.2% | 0.2% | 0.2% | 0.2% | 0.2% |
| PEG-400 | 3% | | | | | |
| B-cyclodextin | | 3% | | | | |
| 1% DOSS solution | | | 0.4% | | | |
| lecithin | | | | 1% | | |
| Tween 20 | | | | | 2% | |
| Tween 80 | | | | | | 2% |
| Ethanol SDA-40B 190 proof (92.3% active) | 62% | 62% | 62% | 62% | 62% | 62% |
| Di-Water | 34.8% | 34.8% | 37.2% | 36.8% | 35.8% | 35.8% |
| Observation | Cloudy solution, Foam disappeared in 20 seconds. | Cloudy solution, Foam disappeared in 20 seconds. | Cloudy solution, Foam disappeared in 20 seconds. | Cloudy solution, Foam disappeared in 20 seconds. | Cloudy solution, Foam disappeared in 20 seconds. | Cloudy solution, Foam disappeared in 20 seconds. |

TABLE 12

Mixing methicone and silicone fluid to improve the foam stability and density.

| | Example 1 | Example 2 | Example 3 | Example 4 | Example 5 | Example 6 |
|---|---|---|---|---|---|---|
| Ethanol SDA-40B 190 proof (92.3% active) | 72.6% | 72.6% | 72.6% | 72.6% | 72.6% | 72.6% |
| PEG-40 Hydrogenated Castor Oil | 3.6% | 3.6% | 3.6% | 3.6% | 3.6% | 3.6% |
| Methyl Methicone (C3) | | | | 0.2% | | 0.05% |
| Caprylyl Methicone (C8 trisiloxane) | 0.2% | 0.2% | 0.2% | | 0.2% | 0.15% |
| Silicone 0.65 cst | | 0.6% | | | | 0.2% |
| Silicone 1 cst | 0.6% | | | 0.6% | 0.6% | 0.4% |
| Silicone 1.5 cst | | | 0.6% | | | |
| PolyOX Ultrez 10 | | | | | | |
| AMP95 | | | | | | |
| Sokalan HP 20 VX 10035 | 1% | 1% | 1% | 1% | 1% | |
| Citric Acid (50%) | 0.3% | 0.3% | 0.3% | 0.3% | 0.3% | 0.3% |
| DI-water | add up to 100% | add up to 100% | add up to 100% | add up to 100% | add up to 100% | add up to 100% |
| Pump 10 times into a 80 ml beaker | Last more than 3 min | Last more than 3 min | Last more than 3 min | Last more than 3 min | Last more than 3 min | Last more than 3 min |

| | Example 7 | Example 8 | Example 9 | Example 10 | Example 11 | Example 12 |
|---|---|---|---|---|---|---|
| Ethanol SDA-40B 190 proof (92.3% active) | 72.6% | 72.6% | 72.6% | 72.6% | 72.6% | 72.6% |
| PEG-40 Hydrogenated Castor Oil | 3.6% | 3.6% | 7.2% | 3.6% | 3.6% | 3.6% |
| Methyl Methicone (C3) | | | | | | |
| Caprylyl Methicone (C8 trisiloxane) | 0.15% | 0.07% | 0.4% | 0.2% | 0.2% | 0.2% |
| Silicone 0.65 cst | | | | | | |
| Silicone 1 cst | 0.65% | 0.75% | 1.2% | 0.6% | 0.6% | 0.6% |
| Silicone 1.5 cst | | | | | | |
| PolyOX Ultrez 10 | 0.08% | 0.08% | | 0.27% | | 0.02% |
| AMP95 | | | | | 0.02% | 0.006% |
| Sokalan HP 20 VX 10035 | | | | | 0.0036% | 0.001% |
| Citric Acid (50%) | 0.3% | 0.3% | | 0.3% | | |
| DI-water | add up to 100% | add up to 100% | add up to 100% | add up to 100% | add up to 100% | add up to 100% |
| Pump 10 times into a 80 ml beaker | Last more than 3 min | Last more than 3 min | Last more than 3 min | Last more than 3 min | Solution cloud with caustic activator | Solution cloud with caustic activator |

See FIG. 5, on the left is Example 1 46 ppm dye without PEG-40, on the right is Example 1 with 46 ppm dye. The Right bottle showed a strong and homogenous fluorescent light indicating that silicone materials (C8 trisiloxane and silicone fluid) have been completely dissolved into ethanol/water solution to form a microemulsion.

The disclosures being thus described, it will be obvious that the same may be varied in many ways. Such variations are not to be regarded as a departure from the spirit and scope of the disclosures and all such modifications are intended to be included within the scope of the following claims. The above specification provides a description of the manufacture and use of the disclosed compositions and methods. Since many embodiments can be made without departing from the spirit and scope of the disclosure, the disclosure resides in the claims.

What is claimed:

1. A foaming surfactant combination capable of reducing surface tension of a water ethanol mixture comprising:
   from about 0.2 to about 0.3 wt. % of a pendent alkyl siloxane; and from about 0.05 to about 0.07 wt. % of a PEG-modified castor oil comprising 20-60 moles of PEG in an ethanol/water solvent mixture comprising from about 62% to about 98% of ethanol.

2. The foaming composition of claim 1, wherein the pendent alkyl siloxane follows the general formula:

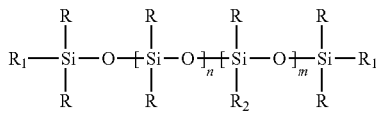

where
n is 0-30;
m is 1-50,
R and R1 are methyl
R2 is linear or branched, unsubstituted or substituted, saturated or unsaturated, aliphatic or aromatic C1-C30 hydrocarbon and is not a hydrophilic group.

3. The foaming composition of claim 2, wherein the pendent alkyl siloxane R2 is a C2 to C28 hydrocarbon, and n is 0 and m is 1.

4. The foaming composition of claim 2, wherein the pendent alkyl siloxane R2 is a C2 to C12 hydrocarbon, n is 0 and m is 1.

5. The foaming composition of claim 2, wherein the pendent alkyl siloxane R2 is a C8 hydrocarbon, n is 0 and m is 1.

6. The foaming composition of claim 2, wherein the pendent alkyl siloxane R2 is a C2 to C28 hydrocarbon, and n is 1 to 30 and m is 1 to 50.

7. The foaming composition of claim 1, wherein the PEG-modified castor oil is hydrogenated.

8. The foaming composition of claim 1, wherein the composition is free of silicone-based surfactants.

9. The foaming composition of claim 1 further comprising from 0.05 wt. % to 0.5 wt. % polyethylene oxide.

10. The foaming composition of claim 1 further comprising from 0.1 wt. % to 5 wt. % of a positively charged polyethyleneimine polymer.

11. The foaming composition of claim 10 wherein the polyethyleneimine polymer is alkoxylated.

12. The foaming composition of claim 11 wherein the polyethyleneimine polymer is ethoxylated.

13. The foaming composition of claim 1 further comprising a dimethyl siloxane with 2-5 Si—O repeating units.

14. The foaming composition of claim 13 wherein the dimethyl siloxane is linear.

15. The foaming composition of claim 13 wherein said dimethyl siloxane is cyclic.

16. A method of hand and hard surface sanitizing, surface cleaning, including rinsing, removing protein, and/or nontransfats through the formation of an emulsion or microemulsion comprising:
applying to a surface having said protein or nontransfat, a cleaning composition/rinse aid comprising:
from about 2 to about 3 wt. % of a pendent alkyl siloxane; and
from about 0.05 to about 0.07 wt. % of a PEG-modified castor oil comprising 20-60 moles of PEG in an ethanol/water solvent mixture comprising from about 62% to about 98% of ethanol.

17. The method of claim 16, further comprising rinsing or wiping said surface so that said protein or trans-fat are removed.

18. The method of claim 16, wherein pendent alkyl siloxane is caprylyl (C8) methicone.

19. The method of claim 16, wherein the PEG-modified castor oil is hydrogenated.

20. The method of claim 16 further comprising from 0.05 wt. % to 0.5 wt. % polyethylene oxide.

21. The method of claim 16 further comprising from 0.1 wt. % to 5 wt. % of a positively charged polyethyleneimine polymer.

22. The method of claim 21 wherein the polyethyleneimine polymer is alkoxylated.

23. The method of claim 21 wherein the polyethyleneimine polymer is ethoxylated.

24. The method of claim 16 wherein said composition further comprises a dimethyl siloxane with 2-5 Si—O repeating units.

25. The method of claim 24 wherein the dimethyl siloxane is linear.

26. The method of claim 24 wherein said dimethyl siloxane is cyclic.

27. A hand sanitizer, hard surface sanitizer or surface cleaning composition comprising:
a foaming component, wherein the foaming component comprises
a) a pendent alkyl siloxane; and
b) a PEG-modified castor oil in an ethanol/water solvent mixture comprising from about 62% to about 98% ethanol.

28. The hand sanitizer, hard surface sanitizer or surface cleaning composition of claim 27, wherein the pendent alkyl siloxane follows the general formula:

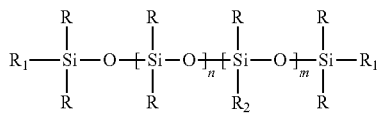

where
n is 0-30;
m is 1-50,
R and R1 are methyl
R2 is linear or branched, unsubstituted or substituted, saturated or unsaturated, aliphatic or aromatic C1-C30 hydrocarbon and is not a hydrophilic group.

29. The hand sanitizer, hard surface sanitizer or surface cleaning composition of claim 28 wherein R2 is a C2 to C28 hydrocarbon, and n is 0 and m is 1.

30. The hand sanitizer, hard surface sanitizer or surface cleaning composition of claim 28 wherein R2 is a C2 to C12 hydrocarbon, n is 0 and m is 1.

31. The hand sanitizer, hard surface sanitizer or surface cleaning composition of claim 28 wherein R2 is a C8 hydrocarbon, n is 0 and m is 1.

32. The hand sanitizer, hard surface sanitizer or surface cleaning composition of claim 28, wherein the pendent alkyl siloxane is caprylyl (C8) methicone.

33. The hand sanitizer, hard surface sanitizer or surface cleaning composition of claim 28, wherein the pendent alkyl siloxane R2 is a C2 to C28 hydrocarbon, and n is 1 to 30 and m is 1 to 50.

34. The hand sanitizer, hard surface sanitizer or surface cleaning composition of claim 27, wherein the PEG-modified castor oil is hydrogenated.

35. The hand sanitizer, hard surface sanitizer or surface cleaning composition of claim 27, wherein the composition is free of silicone-based surfactants.

36. The hand sanitizer, hard surface sanitizer or surface cleaning composition of claim 27 further comprising from 0.05 wt. % to 0.5 wt. % polyethylene oxide.

37. The hand sanitizer, hard surface sanitizer or surface cleaning composition of claim 27 further comprising from 0.1 wt. % to 5 wt. % of a positively charged polyethyleneimine polymer.

38. The hand sanitizer, hard surface sanitizer or surface cleaning composition of claim 37 wherein the polyethyleneimine polymer is alkoxylated.

39. The hand sanitizer, hard surface sanitizer or surface cleaning composition of claim 37 wherein the polyethyleneimine polymer is ethoxylated.

40. The hand sanitizer, hard surface sanitizer or surface cleaning composition of claim 27 further comprising: surfactants, builders, chelating agents, dye transfer inhibiting agents, viscosity modifiers, dispersants, enzymes, and enzyme stabilizers, catalytic materials, bleaches, bleach activators, hydrogen peroxide, sources of hydrogen peroxide, preformed peracids, polymeric dispersing agents, threshold inhibitors for hard water precipitation pigments, clay soil removal/anti-redeposition agents, brighteners, suds suppressors, dyes, fabric hueing agents, perfumes, structure elasticizing agents, fabric softeners, carriers, hydrotropes, processing aids, solvents, pigments antimicrobials, pH buffers, processing aids, active fluorescent whitening ingredient, surfactants and mixtures thereof.

41. The composition of claim 1 wherein said siloxane is a C2-C8 trysiloxane or an ethyl methicone.

* * * * *